United States Patent [19]

Patsch et al.

[11] Patent Number: 5,210,187
[45] Date of Patent: May 11, 1993

[54] DOUBLE ATTACHMENT REACTIVE DYES HAVING ALKYL- OR ALKENYLSULFONYL AND ALKYL- OR ALKENYLSULFONYLALKYL GROUPS

[75] Inventors: Manfred Patsch, Wachenheim; Uwe Nahr, Dannstadt-Schauernheim; Friedrich Wirsing; Joerg L. Jessen, both of Speyer; Klaus Pandl, Ludwigshafen; Claus Marschner, Speyer; Matthias Dust, Ludwigshafen, all of Fed. Rep. of Germany

[73] Assignee: BASF Aktiengesellschaft, Ludwigshafen, Fed. Rep. of Germany

[21] Appl. No.: 865,744

[22] Filed: Apr. 9, 1992

Related U.S. Application Data

[63] Continuation of Ser. No. 554,860, Jul. 20, 1990, abandoned, which is a continuation of Ser. No. 381,941, Jul. 19, 1989, abandoned.

[30] Foreign Application Priority Data

Jul. 28, 1988 [DE] Fed. Rep. of Germany ....... 3825656

[51] Int. Cl.$^5$ ................... C09B 62/04; C09B 62/503; D06P 1/384
[52] U.S. Cl. .................. 534/618; 534/622; 534/632; 534/634; 534/635; 534/637; 534/638; 534/641; 534/642; 540/126; 540/132; 544/76; 549/14; 552/225; 558/25; 558/29; 564/440; 568/29; 568/30
[58] Field of Search ....... 534/618, 634–638, 534/640–644

[56] References Cited

U.S. PATENT DOCUMENTS

Re. 29,640  5/1978  Lamm et al. .................. 534/770
(List continued on next page.)

FOREIGN PATENT DOCUMENTS 197418  10/1986  European Pat. Off. ........... 534/642
0307817  3/1989  European Pat. Off. ........... 534/641
(List continued on next page.)

OTHER PUBLICATIONS

Moser et al, "The Phthalocyanines", vol. 2, CRC Press (1983).
(List continued on next page.)

*Primary Examiner*—Robert W. Ramsuer
*Assistant Examiner*—Fiona T. Powers
*Attorney, Agent, or Firm*—Oblon, Spivak, McClelland, Maier & Neustadt

[57] ABSTRACT

Double attachment reactive dyes have the formula

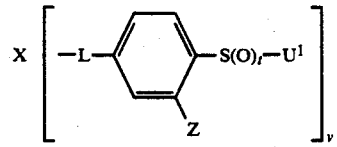

where
$U^1$ is $C_1$–$C_4$-alkyl, phenyl, $C_2$–$C_{10}$-alkenyl or the radical

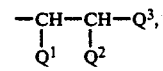

where $Q^1$ and $Q^2$ are each independently of the other hydrogen or $C_1$–$C_4$-alkyl and $Q^3$ is a group which is detachable under alkaline reaction conditions,
Z is the radical

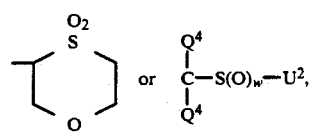

where each $Q^4$ is independently of the other hydrogen or $C_1$–$C_4$-alkyl which may be substituted by cyano, $U^2$ is $C_1$–$C_4$-alkyl, phenyl, $C_2$–$C_{10}$-alkenyl or the radical

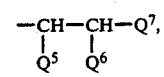

where $Q^5$ and $Q^6$ are each independently of the other hydrogen or $C_1$–$C_4$-alkyl and $Q^7$ is a group which is detachable under alkaline reaction conditions, and w is 0, 1 or 2,
t is 0, 1 or 2,
v is 1 or 2 and X and L are each as defined in the description, with the proviso that at least one of the two radicals $U^1$ and $U^2$ is not $C_1$–$C_4$-alkyl or phenyl, and are prepared from benzyl compounds of the formula

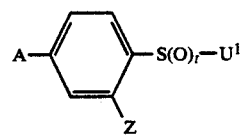

where A is nitro or amino and $U^1$, Z and t are each as defined above.

The reactive dyes are useful for dyeing hydroxyl-containing fibers such as cotton and wool and provide high yields and high wet fastness.

4 Claims, No Drawings

U.S. PATENT DOCUMENTS

| | | | |
|---|---|---|---|
| 3,531,459 | 9/1970 | Chiddix et al. | 534/641 |
| 3,856,772 | 12/1974 | Dunkelman et al. | 534/617 |
| 4,532,237 | 7/1985 | Jager | 544/75 |
| 4,622,390 | 11/1986 | Meininger et al. | 534/637 |
| 4,730,038 | 3/1988 | Meininger et al. | 534/637 |
| 4,812,558 | 3/1989 | Omura et al. | 534/642 X |

FOREIGN PATENT DOCUMENTS

| | | | |
|---|---|---|---|
| 2308663 | 8/1974 | Fed. Rep. of Germany | 534/617 |
| 3119349 | 12/1984 | Fed. Rep. of Germany | 534/642 |
| 3441272 | 5/1986 | Fed. Rep. of Germany | 534/642 |
| 3441273 | 5/1986 | Fed. Rep. of Germany | 534/642 |
| 3441274 | 5/1986 | Fed. Rep. of Germany | 534/642 |
| 1106244 | 3/1968 | United Kingdom | 534/642 |

OTHER PUBLICATIONS

Papenfuhs et al III, Chemical Abstracts, vol. 111, No. 136021a (1989).

Venkataraman, K., "The Chemistry of Synthetic Dyes", vol. 2, Academic Press (1952).

Venkataraman, K., "The Chemistry of Syntheitc Dyes", vol. 3, Academic Press (1970).

Venkataraman, K., "The Chemistry of Synthetic Dyes", vol. 6, Academic Press (1972).

DOUBLE ATTACHMENT REACTIVE DYES HAVING ALKYL- OR ALKENYLSULFONYL AND ALKYL- OR ALKENYLSULFONYLALKYL GROUPS

This application is a Continuation of application Ser. No. 07/554,860, filed on Jul. 20, 1990, now abandoned which is a continuation of U.S. application Ser. No. 07/381,941, filed Jul. 19, 1989 now abandoned.

The present invention relates to double attachment reactive dyes of the formula I $$X\left[-L-\underset{Z}{\underset{|}{\bigcirc}}-S(O)_t-U^1\right]_v \quad (I)$$

where
$U^1$ is $C_1$–$C_4$-alkyl, phenyl, $C_2$–$C_{10}$-alkenyl or the radical $$-CH-CH-Q^3,$$
$$\phantom{-}|\phantom{-CH-}|$$
$$\phantom{-}Q^1\phantom{-CH-}Q^2$$

where $Q^1$ and $Q^2$ are identical or different and each is independently of the other hydrogen or $C_1$–$C_4$-alkyl and $Q^3$ is a group which is detachable under alkaline reaction conditions, Z is the radical $$\begin{array}{c} O_2 \\ S \\ \diagdown \\ \diagup \\ O \end{array} \quad \text{or} \quad \begin{array}{c} Q^4 \\ | \\ C-S(O)_w-U^2, \\ | \\ Q^4 \end{array}$$

where each $Q^4$ is independently of the other hydrogen or $C_1$–$C_4$-alkyl which may be substituted by cyano, $U^2$ is $C_1$–$C_4$-alkyl, phenyl, $C_2$–$C_{10}$-alkenyl or the radical $$-CH-CH-Q^7,$$
$$\phantom{-}|\phantom{-CH-}|$$
$$\phantom{-}Q^5\phantom{-CH-}Q^6$$

where $Q^5$ and $Q^6$ are identical or different and each is independently of the other hydrogen or $C_1$–$C_4$-alkyl and $Q^7$ is a group which is detachable under alkaline reaction conditions, and w is 0, 1 or 2, t is 0, 1 or 2,
v is 0, 1 or 2,
X is a) the radical of a chromophore which may have a further reactive group and which is derived from a mono- or disazo dye, a triphendioxazine, an anthraquinone, a copper formazan or a metallized phthalocyanine, or b) the radical of a coupling component which may additionally be linked to the radical of a diazo component via an azo bridge and which may additionally have a reactive group, and
L is a) a bridge member of the formula $$-\underset{Q^8}{\underset{|}{N}}- \quad \text{or} \quad -\underset{Q^9}{\underset{|}{N}}\overset{N}{\underset{\diagdown}{\diagup}}\underset{Q^{11}}{\underset{\diagup}{\diagdown}}\underset{N}{\overset{|}{N}}\underset{Q^{10}}{\underset{|}{N}}-,$$

where $Q^8$ is hydrogen or $C_1$–$C_4$-alkyl, $Q^9$ and $Q^{10}$ are identical or different and each is independently of the other hydrogen or $C_1$–$C_4$-alkyl and $Q^{11}$ is fluorine, chlorine or bromine, or b) an azo bridge, with the proviso that at least one of the two radicals $U^1$ and $U^2$ is not $C_1$–$C_4$-alkyl or phenyl.

The present invention further relates to novel benzyl compounds which serve as intermediates for these dyes.

EP-A-48,355 and EP-A-65,732 disclose double attachment reactive dyes which are derived from azo dyes having 1-amino-8-hydroxynaphthalene-3,6- or -4,6-disulfonic acid as the coupling component and which have attachment components based on fluorotriazine or chlorotriazine and ring-unsubstituted (sulfonylmethyl)aniline.

Earlier German Patent Application DE-A-3,731,202 relates to double attachment reactive dyes which are derived from metallized or unmetallized azo dyes and have a double attachment system based on a triazine/(-sulfonylmethyl)aniline derivative.

It is an object of the present invention to provide novel double attachment reactive dyes having advantageous application properties.

We have found that this object is achieved with the novel double attachment reactive dyes of the abovementioned formula I.

All the alkyl and alkenyl radicals appearing in the abovementioned formula I can be not only straight-chain but also branched.

If substituted phenyl radicals appear in the above-mentioned formula I, suitable substituents are, unless otherwise stated, for example $C_1$–$C_4$-alkyl, $C_1$–$C_4$-alkoxy and halogen.

$Q^3$ and $Q^7$ in the formula I are each a group which is detachable under alkaline reaction conditions. Such groups are for example chlorine, $OSO_3H$, $SSO_3H$, $OP(O)(OH)_2$, $C_1$–$C_4$-alkylsulfonyloxy, substituted or unsubstituted phenylsulfonyloxy, $C_1$–$C_4$-alkanoyloxy, $C_1$–$C_4$-dialkylamino, $$-\overset{\oplus}{N}\underset{Q^{14}}{\overset{Q^{12}}{\diagup}}-Q^{13}\,An^{\ominus}, \quad -\overset{\oplus}{N}\underset{\diagdown}{\diagup}An^{\ominus},$$

$$-\overset{\oplus}{N}\underset{\diagdown}{\diagup}\overset{CO_2^{\ominus}}{\phantom{N}} \quad \text{or} \quad -\overset{\oplus}{N}\underset{\diagdown}{\diagup}\overset{CONH_2}{\phantom{N}},$$

where $Q^{12}$, $Q^{13}$ and $Q^{14}$ are identical or different and each is independently of the others $C_1$–$C_4$-alkyl or benzyl and each $An^{\ominus}$ is an anion.

$U^1$, $U^2$, $Q^1$, $Q^2$, $Q^4$, $Q^5$, $Q^6$, $Q^8$, $Q^9$, $Q^{10}$, $Q^{12}$, $Q^{13}$ and $Q^{14}$ in the formula I are each for example methyl, ethyl, propyl, isopropyl, butyl, isobutyl or sec-butyl.

$Q^4$ is further for example 2-cyanoethyl or 2- or 3-cyanopropyl.

$U^1$ and $U^2$ in the formula I are each for example 2-chloroethyl, $C_2H_4OSO_3H$, $CH_2$–$CH(CH_3)OSO_3H$, $C_2H_4SSO_3H$, $C_2H_4OP(O)(OH)_2$, 2-(methylsulfonyloxy)ethyl, 2-(ethylsulfonyloxy)ethyl, 2-(propylsulfonyloxy)ethyl, 2-(isopropylsulfonyloxy)ethyl, 2-(butylsulfonyloxy)ethyl, 2(phenylsulfonyloxy)ethyl whose phenyl radical can be substituted for example by $C_1$-$C_4$-alkyl, $C_1$-$C_4$-alkoxy or halogen, 2-(dimethylamino)ethyl, 2-(diethylamino)ethyl, 2-(dipropylamino)ethyl, 2-(diisopropylamino)ethyl, 2-(dibutylamino)ethyl, 2-(N-methyl-N-ethylamino)ethyl, vinyl, prop-1-en-1-yl, prop-1-en-3-yl or but-2-en-2-yl.

$U^1$ and $U^2$ are each further for example 2-(trimethylammonium)ethyl, 2-(triethylammonium)ethyl, 2-(methyldiethylammonium)ethyl, 2-(tripropylammonium)ethyl, 2-(methyldipropylammonium)ethyl, 2-(tributylammonium)-ethyl, 2-(benzyldimethylammonium)ethyl, 2-(benzyl-diethylammonium)ethyl, 2-pyridiniumethyl or 2-(2-, 3- or 4-carboxylatopyridinium)ethyl, in which case (except for the 2-(2-, 3- or 4-carboxylatopyridinium)ethyl radical, which is present as a betaine) a suitable anion $Ar^{\ominus}$ is for example fluoride, chloride, bromide, iodide, mono-, di or trichloroacetate, methylsulfonate, phenylsulfonate or 2- or 4-methylphenylsulfonate.

The fiber-reactive double attachment radical of the formula II

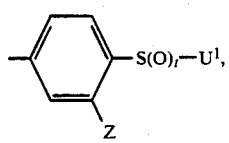

(II)

where $U^1$, Z and t are each as defined above, will hereinafter be referred to as "E".

Preference is given to double attachment reactive dyes of the formula Ia $X[-L-E]_v$ (Ia)

where X, L and v are each as defined above and $E^1$ is a radical of the formula IIa

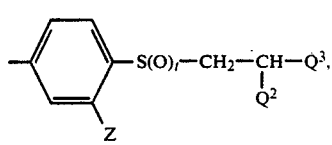

(IIa)

where
$Q^2$ is hydrogen or methyl,
$Q^3$ is $OSO_3H$,
Z is the radical

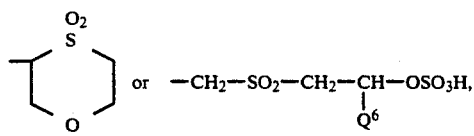

where $Q^6$ is hydrogen or methyl, and
t is 0 or 2.

Particular preference is given to double attachment reactive dyes of the formula Ib $X[-L-E]_v$ (Ib)

where X, L and v are each as defined above and $E^2$ is a radical of the formula IIb

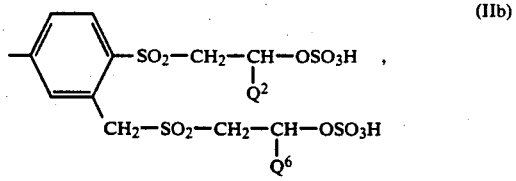

(IIb)

where $Q^2$ and $Q^6$ are each independently of the other hydrogen or methyl.

Very particular preference is given to double attachment reactive dyes of the formula Ic $X[-L-E]_v$ (Ic)

where X, L and v are each as defined above and $E^3$ is the radical of the formula IIc

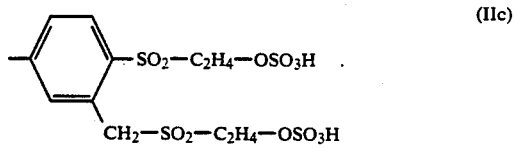

(IIc)

Besides the double attachment system E, the radical X may carry further fiber-reactive radicals. Such radicals are derived for example from triazine, pyrimidine or vinylsulfonyl compounds.

X in the formula I is for example the radical of a coupling component which may additionally be linked to the radical of a diazo component via an azo bridge and which may have an additional reactive group. In this case, the double attachment radical E is bonded to the radical X via an azo bridge (—N=N—).

Dyes of this class conform to the formula IVa or IVb $(E-N=N-)_aK$ (IVa)

or $E-N=N-K-N=N-D$ (IVb), where K is the radical of a coupling component, D is the radical of a diazo component, a is 1 or 2, and E is as defined above.

Useful dyes of this class are for example water-soluble azo dyes, in particular monoazo dyes of the formula IVa (a=1) or disazo dyes of the formula IVb which have hydroxysulfonyl and/or carboxyl groups.

Important coupling components HK are derived for example from compounds of the benzene, naphthalene, pyrazolone, pyridone or hydroxypyrimidine series.

Important diazo components $D-NH_2$ are derived for example from compounds of the aniline or aminonaphthalene series.

Particular preference is given to dyes of the formula V $E^1-N=N-K^1$ (V), where $E^1$ is as defined above and $K^1$ is the radical of a coupling component of the naphthalene, pyrazole, pyridone or hydroxypyrimidine series which may be a further fiber-reactive group.

Particular preference is further given to dyes of the formula VI

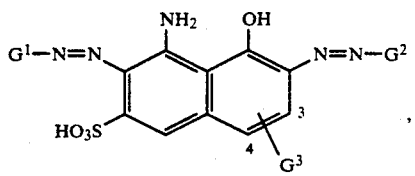 (VI)

where one of the two radicals $G^1$ and $G^2$ is $E^1$ of the abovementioned meaning and the other is $D^1$ in the meaning of a radical of a diazo component of the aniline or naphthalene series which may have a further fiber-reactive group, and $G^3$ is hydroxysulfonyl in ring position 3 or 4.

X in the formula I is further for example a metallized or unmetallized radical of an azo dye. Suitable azo dye radicals are known per se and have been described in large numbers, for example in K. Venkataraman, The Chemistry of Synthetic Dyes, vol. VI, Academic Press, New York, London, 1972. The azo dyes conform to the formula VII

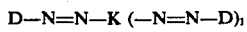 (VII)

where D is the radical of a diazo component, K is the radical of a coupling component and l is 0 or 1.

Useful dyes are for example water-soluble azo dyes, in particular monoazo dyes, of the formula VII (l=0) which can have hydroxysulfonyl and/or carboxyl groups.

Preference is given to nonmetallized azo dyes, in particular those which contain sulfo and/or carboxyl groups, especially those having from 1 to 6 sulfo groups.

Important azo dyes are for example those of the benzene-azo-naphthalene, benzene-azo-1-phenylpyrazol-5-one, benzene-azo-benzene, naphthalene-azo-benzene, benzene-azo-aminonaphthalene, naphthalene-azonaphthalene, naphthalene-azo-1-phenylpyrazol-5-one, benzene-azo-pyridone, benzene-azo-aminopyridine, naphthalene-azo-pyridone, naphthalene-azo-aminopyridine or stilbene-azo-benzene series.

Particular preference is given to double attachment reactive dyes of the formula VIII

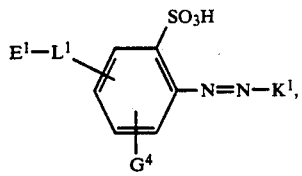 (VIII)

where $E^1$ is as defined above,
$L^1$ is the radical

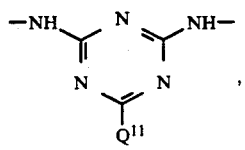

where $Q^{11}$ is as defined above, $G^4$ is hydrogen, $C_1$-$C_4$-alkyl, chlorine or hydroxysulfonyl, and $K^1$ is the radical of a coupling component of the naphthalene, pyrazolone, pyridone or hydroxypyrimidine series which may have a further fiber-reactive group.

Particular preference is further given to double attachment reactive dyes of the formula IX

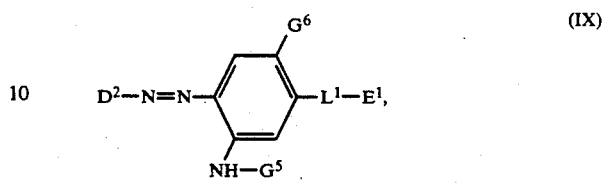 (IX)

where $E^1$ and $L^1$ are each as defined above, $G^5$ is $C_1$-$C_4$-alkanoyl, carbamoyl, $C_1$-$C_4$-mono- or -di-alkylcarbamoyl, phenylcarbamoyl or cyclohexylcarbamoyl, $G^6$ is hydrogen, $C_1$-$C_4$-alkyl, $C_1$-$C_4$-alkoxy, hydroxysulfonyl or chlorine, and $D^2$ is the radical of a diazo component of the aniline or naphthalene series which does not carry any further fiber-reactive group.

Particular preference is further given to double attachment reactive dyes of the formula X

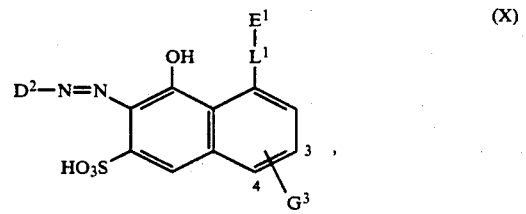 (X)

where $D^2$, $E^1$ and $L^1$ are each as defined above and $G^3$ is hydroxysulfonyl in ring position 3 or 4.

Particular preference is further given to double attachment reactive dyes of the formula XI

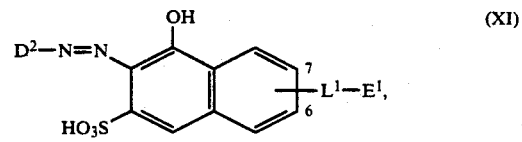 (XI)

where $D^2$, $E^1$ and $L^1$ are each as defined above and the group —L—$E^1$ is in ring position 6 or 7.

Furthermore, useful compounds are those of the formula XII

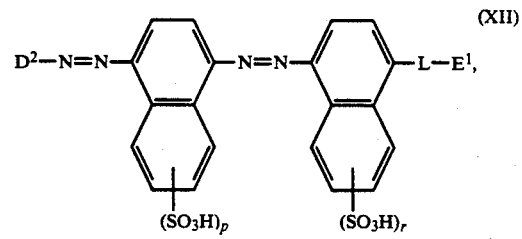 (XII)

where $D^2$, $E^1$ and $L^1$ are each as defined above and p and r are each 0, 1 or 2.

Furthermore, useful dyes are those of the formula XIII

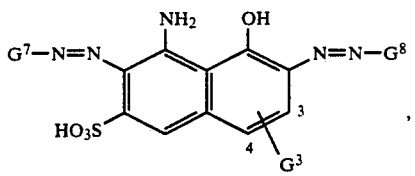 (XIII)

where $G^3$ is as defined above and one of the two radicals $G^7$ and $G^8$ is $D^2$ of the abovementioned meaning and the other is the radical $SO_3H$

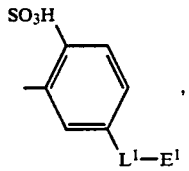

where $L^1$ and $E^2$ are each as defined above.

Such aromatic radicals D of diazo components of the aniline and aminonaphthalene series which do not carry any fiber-reactive groups are derived for example from amines of the formulae XIV a-f

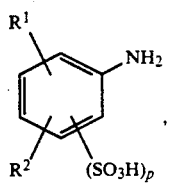 (XIVa)

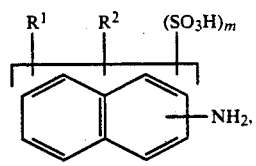 (XIVb)

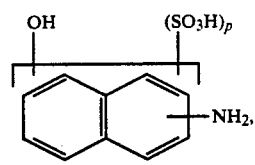 (XIVc)

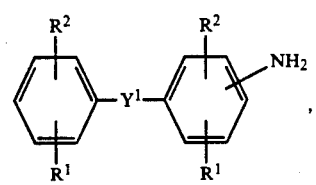 (XIVd)

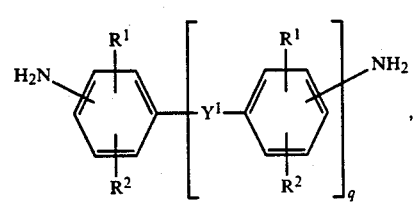 (XIVe)

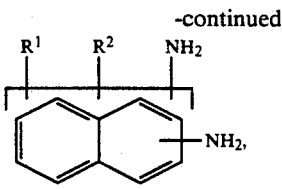 (XIVf)

where
m is 0, 1, 2 or 3,
p is 0, 1 or 2,
q is 0 or 1,
$R^1$ is hydrogen, methyl, ethyl, methoxy, ethoxy, acetyl, cyano, carboxyl, hydroxysulfonyl, $C_1$-$C_4$-alkoxycarbonyl, hydroxyl, carbamoyl, $C_1$-$C_4$-mono- or -dialkylcarbamoyl, fluorine, chlorine, bromine or trifluoromethyl,
$R^2$ is hydrogen, methyl, ethyl, methoxy, ethoxy, cyano, carboxyl, hydroxysulfonyl, acetylamino, $C_1$-$C_4$-alkoxycarbonyl, carbamoyl, $C_1$-$C_4$-mono- or -dialkylcarbamoyl, fluorine, chlorine, nitro, sulfamoyl, $C_1$-$C_4$-mono- or -di-alkylsulfamoyl, $C_1$-$C_4$-alkylsulfonlyl, phenylsulfonyl or phenoxy and
$Y^1$ is a direct bond, oxygen, sulfur or the group —NH—CO—, —CONH—, —CO—, —NHSO$_2$—, —SO$_2$NH—, —SO$_2$—, —CH═CH—, —CH$_2$—CH$_2$—, —CH$_2$—, —NH— or —N═N—.

Preference is given to those components where $R^1$ is hydrogen, methyl, methoxy, carboxyl, hydroxysulfonyl, hydroxyl or chlorine, $R^2$ is hydrogen, methyl, methoxy, carboxyl, hydroxysulfonly, acetylamino or chlorine and $Y^1$ is the group —CO—, —SO$_2$—, —CH═CH—, —CH$_2$—CH$_2$—, —CH$_2$— or —N═N—.

Aromatic amines which are suitable for use as diazo components and which conform to the formula XIVa, XIVb, XIVc or XIVd are for example aniline, 2-methoxyaniline, 2-methylaniline, 4-chloro-2-aminoanisole, 4-methylaniline, 4-methoxyaniline, 2-methoxy-5-methylaniline, 2,5-dimethoxyaniline, 2,5-dimethylaniline, 2,4-dimethylaniline, 4-butylaniline, 2,5-diethoxyaniline, 2-chloroaniline, 3-chloroaniline, 4-chloroaniline, 2,5-dichloroaniline, 4-chloro-2-nitroaniline, 4-chloro-2-methylaniline, 3-chloro-2-methylaniline, 4-chloro-2-aminotoluene, 4-(p-tolylsulfonyl)aniline, 2-ethoxy-1-naphthylamine, 1-naphthylamine, 2-naphthylamine, 4-benzoylamino-2ethoxyaniline, 4-methylsulfonylaniline, 2,4-dichloroaniline-5-carboxylic acid, 2-aminobenzoic acid, 4-aminobenzoic acid, 3-aminobenzoic acid, 3-chloroaniline-6-carboxylic acid, aniline-2- or -3- or -4-sulfonic acid, aniline-2,5-disulfonic acid, aniline-2,4-disulfonic acid, aniline-3,5-disulfonic acid, 2-aminotoluene-4-sulfonic acid, 2-aminoanisole-4-sulfonic acid, 2-aminoanisole-5-sulfonic acid, 2-ethoxyaniline-5-sulfonic acid, 2-ethoxyaniline-4-sulfonic acid, 4-hydroxysulfonyl-2-aminobenzoic acid, 2,5-dimethoxyaniline-4-sulfonic acid, 2,4-dimethoxyaniline-5-sulfonic acid, 2-methoxy-5-methylaniline-4-sulfonic acid, 4-aminoanisole-3-sulfonic acid, 4-aminotoluene-3-sulfonic acid, 2-aminotoluene-5-sulfonic acid, 2-chloroaniline-4-sulfonic acid, 2-chloroaniline-5-sulfonic acid, 2-bromoaniline-4-sulfonic acid, 2,6-dichloroaniline-4-sulfonic acid, 2,6-dimethylaniline-3-or -4-sulfonic acid, 3-acetylamino-6-sulfonic acid, 4-acetylamino-2-hydroxysulfonylaniline, 1-aminonaphthalene-4-sulfonic acid, 1-aminonaphthalene-3-sulfonic acid, 1-aminonaphthalene-5-sulfonic acid, 1-aminonaphthalene-6-sulfonic acid, 1-aminonaphthalene-7-sulfonic acid, 1-aminonaphthalene-3,7-disulfonic acid, 1-aminonaphthalene-3,6,8-trisulfonic acid, 1-aminonaphthalene-4,6,8-trisulfonic acid, 2-naphthylamine-5-sulfonic acid or -6- or -8-sulfonic acid, 2-aminonaphthalene-3,6,8-trisulfonic acid, 2-aminonaphthalene-6,8-disulfonic acid, 2-aminonaphthalene-1,6-disulfonic acid, 2-aminonaphthalene-1-sulfonic acid, 2-aminonaphthalene-1,5-disulfonic acid, 2-aminonaphthalene-3,6-disulfonicacid,2-aminonaphthalene-4,8-disulfonic acid, 2-aminophenol-4-sulfonic acid, 2-aminophenol-5-sulfonic acid, 3-aminophenol-6-sulfonic acid, 1-hydroxy-2-aminonaphthalene-5,8-or-4,6-disulfonic acid, 4-aminodiphenylamine, 4-amino-4'-methoxydiphenylamine, 4-amino-4'-methoxydiphenylamine-3-sulfonic acid, 4-(2'-methylphenylazo)-2-methylaniline, 4-aminoazobenzene, 4'-nitrophenylazo-1-aminonaphthalene, 4-(6'-hydroxysulfonylnaphthylazo)-1-aminonaphthalene, 4-(2',5'-dihydroxysulfonylphenylazo)-1-aminonaphthalene, 4'-amino-3'-methyl-3-nitrobenzophenone, 4-aminobenzophenone, 4-(4'-aminophenylazo)benzenesulfonic acid, 4-(4'-amino-3'methoxyphenylazo)benzenesulfonic acid and 2-ethoxy-1-naphthylamine-6-sulfonic acid.

Aromatic diamines which are suitable for use as tetrazo components and which conform to the formula XIVe or XIVf are for example 1,3-diaminobenzene, 1,3-diaminobenzene-4-sulfonic acid, 1,4-diaminobenzene, 1,4-diaminobenzene-2-sulfonic acid, 1,4-diamino-2-methylbenzene, 1,4-diamino-2-methoxybenzene, 1,3-diamino-4-methylbenzene, 1,3-diaminobenzene-5-sulfonic acid, 1,3-diamino-5-methylbenzene, 1,6-diaminonaphthalene-4-sulfonic acid, 2,6-diaminonaphthalene-4,8-disulfonicacid,3,3'-diaminodiphenyl sulfone, 4,4'-diaminodiphenyl sulfone, 4,4'-diaminostilbene-2,2'-disulfonic acid, 2,7'-diaminodiphenyl sulfone, 2,7'-diamino-4,5-disulfodiphenyl sulfone, 4,4'-diaminobenzophenone, 4,4'-diamino-3,3'-dinitrobenzophenone, 3,3'-diamino-4,4'-dichlorobenzophenone, 4,4'- or 3,3'-diaminobiphenyl, 4,4'-diamino-3,3'-dichlorobiphenyl, 4,4'-diamino-3,3'-dimethoxy- or -3,3'-dimethyl- or -2,2'-dimethyl- or -2,2'-dichloro- or -3,3'-diethoxy-biphenyl, 4,4'-diamino-3,3'-dimethyl-6,6'-dinitrobiphenyl, 4,4'-diaminobiphenyl-2,2'- or -3,3'-disulfonic acid, 4,4'-diamino-3,3'-dimethyl- or -3,3'-dimethoxy- or -2,2'-dimethoxy-biphenyl-6,6'-disulfonic acid, 4,4'-diamino-2,2',5,5'-tetrachlorobiphenyl, 4,4'-diamino-3,3'-dinitrobiphenyl, 4,4'-diamino-2,2'-dichloro-5,5'-dimethoxybiphenyl, 4,4'-diaminobiphenyl-2,2'- or -3,3'-dicarboxylic acid, 4,4'-diamino-3,3'-dimethylbiphenyl-5,5'-disulfonic acid, 4,4'-diamino-2-nitrobiphenyl, 4,4'-diamino-3-ethoxy- and -3-hydroxy-sulfonylbiphenyl, 4,4'-diamino-3,3'-dimethylbiphenyl-5-sulfonic acid, 4,4'-diaminodiphenylmethane, 4,4'-diamino-3,3'-dimethyldiphenylmethane, 4,4'-diamino-2,2',3,3'-tetramethyldiphenylmethane, 4,4'-diaminodiphenylethane,4,4'-diaminostilbene and 4,4'-diaminodiphenylmethane-3,3'-dicarboxylic acid.

Aromatic radicals D of diazo components of the aniline or aminonaphthalene series which can carry a fiber-reactive radical E are derived for example from amines of the formulae XVa-c

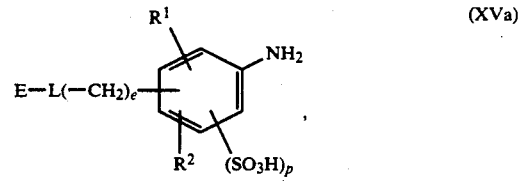

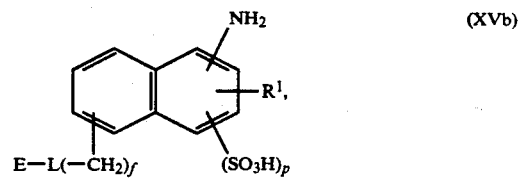

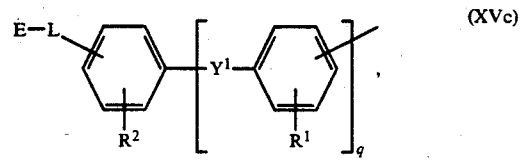

where L, $R^1$, $R^2$, p, q, $Y^1$ and E are each as defined above and e and f are identical or different and each is independently of the other 0 or 1.

Aromatic amines which conform to the formula XVa, XVb or XVc are for example 1,3-diaminobenzene, 1,3-diaminobenzene-4-sulfonic acid, 1,3-diaminobenzene-4,6-disulfonic acid, 1,4-diaminobenzene, 1,4-diaminobenzene-2-sulfonic acid, 1,4-diaminobenzene-2,5-disulfonic acid, 1,4-diamino-2-methylbenzene, 1,4-diamino-2-methoxybenzene, 1,3-diamino-4-methylbenzene, 1,4-diaminobenzene-2,6-disulfonic acid, 1,5-diamino-4-methylbenzene-2-sulfonic acid, 1,5-diamino-4-methoxybenzene-2-sulfonic acid, 1,6-diaminonaphth-2-ol-4-sulfonic acid, 1,6-diaminonaphthalene-4-sulfonic acid, 2,6-diaminonaphthalene-4,8-disulfonic acid, 2,6-diaminonaphth-1-ol-4,8-disulfonic acid, 1,3-diaminobenzene-5-sulfonic acid, 1,3-diamino-5-methylbenzene, 2,6-diaminophenol-4-sulfonic acid, 5-(aminomethyl)-2-aminonaphthalene-1-sulfonic acid, 5-(N-methylaminomethyl)-2-aminonaphthalene-1-sulfonic acid, 4,4'-diaminostilbene-3,3-dicarboxylic acid, 4-(N-methylaminomethyl)aniline-2-sulfonic acid and 3-(N-methylaminomethyl)aniline-6-sulfonic acid.

The radicals K of the coupling component preferably come from the aniline, naphthalene, pyrazole, pyridine, pyrimidine, indole or acylacetarylide series and may also carry fiber-reactive groups.

Coupling components of the aniline and naphthalene series which are free of fiber-reactive groups correspond for example to compounds of the formulae XVIa-g

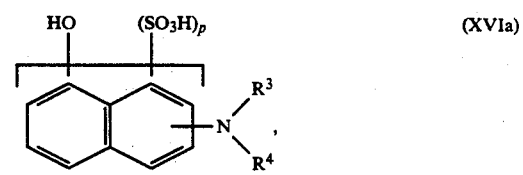

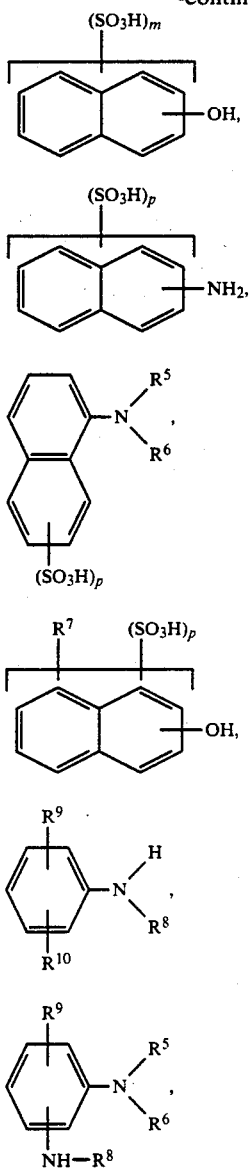

where
R³ is hydrogen or C₁-C₄-alkyl,
R⁴ is hydrogen, C₁-C₄-alkyl or phenyl which may be monosubstituted or disubstituted by C₁-C₄-alkyl, C₁-C₄-alkoxy, chlorine, bromine or hydroxysulfonyl,
R⁵ is hydrogen or C₁-C₄-alkyl which may be substituted by hydroxyl, cyano, carboxyl, hydroxysulfonyl, hydroxysulfonyloxy, methoxycarbonyl, ethoxycarbonyl or acetoxy,
R⁶ is hydrogen, C₁-C₄-alkyl which may be substituted by hydroxyl, cyano, carboxyl, hydroxysulfonyl, hydroxysulfonyloxy, methoxycarbonyl, ethoxycarbonyl or acetoxy, benzyl or phenyl which may be substituted by C₁-C₄-alkyl, C₁-C₄-alkoxy, chlorine or hydroxysulfonyl,
R⁷ is C₁-C₆-alkylureido, phenylureido which may be substituted by chlorine, methyl, methoxy, nitro, hydroxysulfonyl or carboxyl, C₁-C₆-alkanoylamino, cyclohexanoylamino, benzoylamino which may be substituted by chlorine, methyl, methoxy, nitro, hydroxysulfonyl or carboxyl, or hydroxyl, R⁸ is hydrogen, C₁-C₆-alkyl, in particular C₁-C₄-alkyl, which may each be substituted by phenyl, C₁-C₄-alkoxy, hydroxyl, phenoxy or C₁-C₄-alkanoyloxy, C₅-C₇-cycloalkyl, hydroxysulfonylphenyl, C₁-C₄-alkanoyl, carbamoyl, C₁-C₄-mono- or -di-alkylcarbamoyl, phenylcarbamoyl or cyclohexylcarbamoyl,
R⁹ is methoxy, ethoxy, chlorine, bromine, acetylamino, amino, ureido, methylsulfonylamino, ethylsulfonylamino, dimethylaminosulfonylamino, methylamino, ethylamino, dimethylamino or diethylamino,
R¹⁰ is hydrogen, methyl, ethyl, methoxy, ethoxy, chlorine or bromine, and
p and m are each as defined above.

Specific examples are aniline-N-methanesulfonate, o- or m-toluidine, o- or m-anisidine, cresidine, 2,5-dimethylaniline, 2,5-dimethoxyaniline, m-aminoacetanilide, 3-amino-4-methoxyacetanilide, 3-amino-4-methylacetanilide, m-aminophenylurea, N-methylaniline, N-methyl-m-toluidine, N-ethylaniline, N-ethyl-m-toluidine, N-(2-hydroxyethyl)aniline and N-(2-hydroxyethyl)-m-toluidine.

Naphtholsulfonic acids are for example 1-naphthol-3-sulfonic acid, 1-naphthol-4-sulfonic acid, 1-naphthol-5-sulfonic acid, 1-naphthol-8-sulfonic acid, 1-naphthol-3,6-disulfonic acid, 1-naphthol-3,8-disulfonic acid, 2-naphthol-5-sulfonic acid, 2-naphthol-6-sulfonic acid, 2-naphthol-7-sulfonic acid, 2-naphthol-8-sulfonic acid, 2-naphthol-3,6-disulfonic acid, 2-naphthol-6,8-disulfonic acid, 2-naphthol-3,6,8-trisulfonic acid, 1,8-dihydroxynaphthalene-3,6-disulfonic acid, 2,6-dihydroxynaphthalene-8-sulfonic acid and 2,8-dihydroxynaphthalene-6-sulfonic acid.

Further examples are 1-naphthylamine, N-phenyl-1-napthtylamine, N-ethyl-1-naphthylamine, N-phenyl-2-naphthylamine, 1,5-naphthylenediamine, 1,8-naphthylenediamine, 1-naphthol, 2-naphthol, 1,5-dihydroxynaphthalene, 1,6-dihydroxynaphthalene,1,7-dihydroxynaphthalene, 2,7-dihydroxynaphthalene, 2-hydroxynaphthalene-3-N-phenylcarboxamide, 2-hydroxynaphthalene-3-N-(2'-methoxyphenyl)carboxamide and 2-hydroxynaphthalene-3-N-(2',5'-dimethoxyphenyl)-carboxamide.

Aminonaphthalenesulfonic acids are for example 1-naphthylamine-6-sulfonicacid,1-naphthylamine-7-sulfonic acid, 1-naphthylamine-8-sulfonic acid, 2-naphthylamine-3,6-disulfonic acid, 2-naphthylamine-5,7-disulfonic acid and 2-naphthylamine-6,8-disulfonic acid.

Specific aminonaphtholsulfonic acids are for example 1-amino-5-hydroxynaphthalene-7-sulfonic acid, 1-amino-8-hydroxynaphthalene-4-sulfonic acid, 1-amino-8-hydroxynaphthalene-2,4-disulfonic acid, 1-amino-8-hydroxynaphthalene-3,6-disulfonic acid, 1-amino-8-hydroxynaphthalene-4,6-disulfonic acid, 2-amino-5-hydroxynaphthalene-7-sulfonic acid, 2-amino-8-hydroxynaphthalene-6-sulfonic acid, 2-amino-8-hydroxynaphthalene-3,6-disulfonic acid, 2-amino-5-hydroxynaphthalene-1,7-disulfonic acid, 1-acetylamino-8-hydroxynaphthalene-3,6-disulfonic acid, 1-benzoylamino-8-hydroxynaphthalene-3,6-disulfonic acid, 1-acetylamino-8-hydroxynaphthalene-4,6-disulfonic acid, 1-benzoylamino-8-hydroxynaphthalene-4,6-disulfonic acid, 1-acetylamino-5-hydroxynaphthalene-7-sulfonic acid, 2-methylamino-8-hydroxynaphthalene-6-sulfonic acid, 2-methylamino-8-hydroxynaphthalene-6-sulfonic acid and 2-(3'- or 4'-hydroxysulfonylphenyl)amino-8-hydroxynaphthalene-6-sulfonic acid.

Of particular importance are coupling components which have sulfo and/or carboxyl groups and which couple ortho or para to a hydroxyl and/or amino group.

Examples of such coupling components are 2-acetylamino-5-hydroxynaphthalene-7-sulfonic acid, 2-acetylamino-8-hydroxynaphthalene-6-sulfonic acid, 1-acetylamino-8-hydroxynaphthalene-3,6-disulfonic acid, 1-benzoylamino-8-hydroxynaphthalene-3,6-disulfonic acid, 1-acetylamino-8-hydroxynaphthalene-4,6-disulfonic acid and 1-benzoylamino-8-hydroxynaphthalene-4,6-disulfonic acid.

Coupling components of the other series are for example: pyrazolones, aminopyrazoles, 2,6-diaminopyridines, pyridones, hydroxypyrimidines, aminopyrimidines indoles and acetaoacetarylides.

Coupling components of this series which are free of fiber-reactive groups conform for example to the formulae XVIIa-f

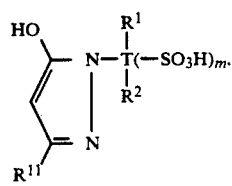 (XVIIa)

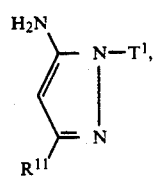 (XVIIb)

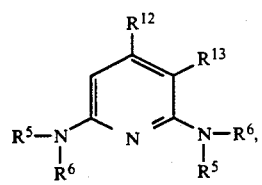 (XVIIc)

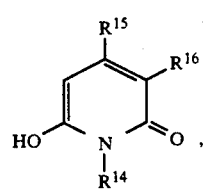 (XVIId)

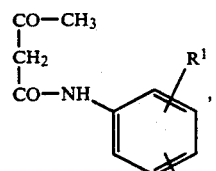 (XVIIe)

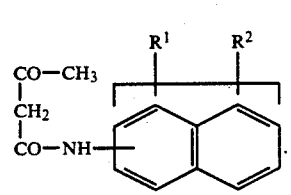 (XVIIf)

where
T is a benzene or naphthalene nucleus, $T^1$ is $C_1$-$C_4$-alkyl, cyclohexyl, benzyl or phenyl which is monosubstituted or polysubstituted by fluorine, chlorine, bromine, methyl, methoxy, nitro, hydroxysulfonyl, carboxyl, acetyl, acetylamino, methylsulfonyl, sulfamoyl or carbamoyl, $R^{11}$ is methyl, carboxyl, methoxycarbonyl, ethoxycarbonyl or phenyl, $R^{12}$ is hydrogen or $C_1$-$C_4$-alkyl which may be substituted by methoxy, ethoxy or cyano, $R^{13}$ is hydrogen, methyl, hydroxysulfonylmethyl, hydroxysulfonyl, cyano or carbamoyl, $R^{14}$ is hydrogen, $C_1$-$C_4$-alkyl which may be substituted by phenyl, hydroxysulfonylphenyl, hydroxyl, amino, methoxy, ethoxy, carboxyl, hydroxysulfonyl, acetylamino, benzoylamino or cyano, cyclohexyl, phenyl which may be substituted by carboxyl, hydroxysulfonyl, benzoylamino, acetylamino, methyl, methoxy, cyano or chlorine, or amino which is substituted by phenyl, $C_1$-$C_4$-alkyl, acetyl or benzoyl, $R^{15}$ is $C_1$-$C_4$-alkyl, phenyl, hydroxyl, cyano, acetyl, benzoyl, carboxyl, methoxycarbonyl, carbamoyl or hydroxysulfonylmethyl, $R^{16}$ is hydrogen, chlorine, bromine, acetylamino, amino, nitro, hydroxysulfonyl, sulfamoyl, methylsulfonyl, phenylsulfonyl, carboxyl, methoxycarbonyl, acetyl, benzoyl, carbamoyl, cyano or hydroxysulfonylmethyl, and $R^1$, $R^2$, $R^5$, $R^6$ and m are each as defined above.

Pyrazolone coupling components are for example 3-methyl-, 3-carboxy- or 3-($C_1$-$C_4$-alkoxycarbonyl)-pyrazol-5-ones which may carry in the 1-position hydrogen, unsubstituted or methyl-, ethyl-, fluorine-, chlorine-, bromide-, -trifluoromethyl-, methoxy-, ethoxy-, cyano-, phenoxy-, phenylsulfonyl-, methylsulfonyl-, hydroxysulfonyl-, benzoyl-, acetyl-, acetylamino-, nitro-, hydroxyl-, carboxyl-, carbamoyl- or sulfamoyl-substituted phenyl or hydroxysulfonyl-substituted 1- or 2-naphthyl. Specific examples are 1-phenyl-, 1-(2,-chlorophenyl)-, 1-(2'-methoxyphenyl)-, 1-(2'-methylphenyl)-, 1-(1',5'-dichlorophenyl)-, 1-(2',6'-dichlorophenyl)-, 1-(2'-methyl-6'-chlorophenyl)-, 1-(2'-methoxy-5'-methylphenyl)-, 1-(2'-chloro-5'-hydroxysulfonylphenyl)-, 1-(2'-methoxy-5'-hydroxysulfonylphenyl)-, 1-(2',5'-dichloro-4'-hydroxysulfonylphenyl)-, 1-(2',5'-dihydroxysulfonylphenyl)-,1-(2'-carboxyphenyl)-, 1-(3'-hydroxysulfonylphenyl)-, 1-(4'-hydroxysulfonylphenyl)- or 1-(3'-sulfamoylphenyl)-3-carboxyl-pyrazol-5-one, 1-(3'- or 4'-hydroxysulfonylphenyl), 1-(2'-chlorophenyl)-, 1-(2'-chloro-4'- or -5'-hydroxysulfonylphenyl)-, 1-(2'-methyl-4'-hydroxysulfonylphenyl), 1-(2',5'-dichlorophenyl)-, 1-(4',8'-dihydroxysulfonyl-8-naphthyl)-or 1-(6'-hydroxysulfonyl-1-naphthyl)-3-methylpyrazol-5-one, ethyl-1-phenylpyrazol-5-one-3-carboxylate, ethyl pyrazol-5-one-3-carboxylate and pyrazol-5-one-3-carboxylic acid.

Other coupling components from the pyrazole series are for example 1-methyl-, 1-ethyl-, 1-propyl-, 1-butyl-, 1-cyclohexyl-, 1-benzyl- or 1-phenyl-5-aminopyrazole, 1-(4'-chlorophenyl)- or 1-(4'-methylphenyl)-5-aminopyrazole and 1-phenyl-3-methyl-5-aminopyrazole.

Acetoacetanilides are in particular acetoacetanilide itself and derivatives thereof with one or more chlorine, methyl, ethyl, methoxy, ethoxy, acetylamino, hydroxysulfonyl, carboxyl, carbamoyl or sulfamoyl substituents in the phenyl nucleus.

Pyridine-based coupling components are for example the derivatives described in DE-A-2,260,827.

Suitable pyrimidine coupling components are for example the compounds listed in DE-A-2,202,820, DE-A-2,308,663 and DE-A-3,119,349. It is also possible to use barbituric acid and N-substitution products thereof. Suitable N-substituents here are in particular $C_1$–$C_4$-alkyl and substituted or unsubstituted phenyl.

Suitable indole coupling components are for example 2-methylindole, 2-phenylindole, 2-phenylindole-5-sulfonic acid, 1-methyl-2-phenylindole and 1-(2'-hydroxyethyl)-, 1-(2'-carboxyethyl)- or 1-(2'-carbamoylethyl)-2-methylindole or -2-phenylindole.

Suitable pyridone coupling components are for example 1-ethyl-2-hydroxy-4-methyl-5-carbamoylpyrid-6-one, 1-(2'-hydroxyethyl)-2-hydroxy-4-methyl-5-carbamoylpyrid-6-one, 1-phenyl-2-hydroxy-4-methyl-5-carbamoylpyrid-6-one, 1-ethyl-2-hydroxy-4-methyl-5-cyanopyrid-6-one, 1-ethyl-2-hydroxy-4-hydroxysulfonylmethyl-5-carbamoylpyrid-6-one, 1-ethyl-2-hydroxy-4-methyl-5-hydroxysulfonylmethylpyrid-6-one, 1-methyl-2-hydroxy-4-methyl-5-cyanopyrid-6-one, 1-methyl-2-hydroxy-5-acetylpyrid-6-one, 1,4-dimethyl-2-hydroxy-5-cyanopyrid-6-one, 1,4-dimethyl-5-carbamoylpyrid-6-one, 2,6-dihydroxy-4-ethyl-5-cyanopyridine, 2,6-dihydroxy-4ethyl-5-carbamoylpyridine, 1-ethyl-2-hydroxy-4-methyl-5-hydroxysulfonylmethylpyrid-6-one, 1-methyl-2-hydroxy-4-methyl-5-methylsulfonylpyrid-6-one and 1-carboxymethyl-2-hydroxy-4-ethyl-5-phenylsulfonylpyrid-6-one.

Coupling components K of the aniline and naphthalene series which contain fiber-reactive groups are for example compounds of the formulae XVIIIa-e

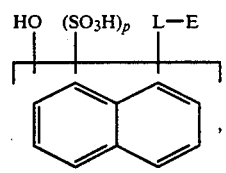 (XVIIIa)

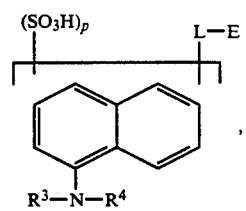 (XVIIIb)

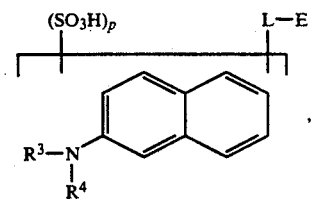 (XVIIIc)

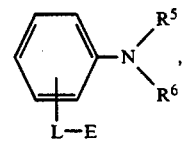 (XVIIId)

and

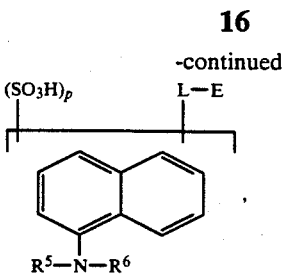 (XVIIIe)

where L, $R^3$, $R^4$, $R^5$, $R^6$, E and p are each as defined above.

Coupling components of the pyrazolone, aminopyrazole, 2,6-diaminopyridine, pyridone, hydroxy or aminopyrimidine, indole or acetoacetarylide series which contain fiber-reactive groups conform for example to the formulae XIXa-f

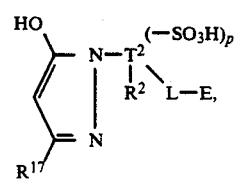 (XIXa)

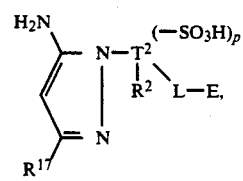 (XIXb)

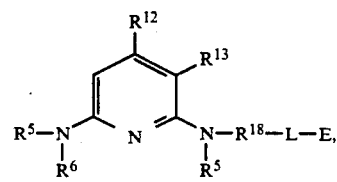 (XIXc)

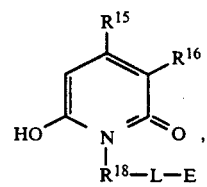 (XIXd)

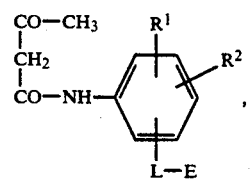 (XIXe)

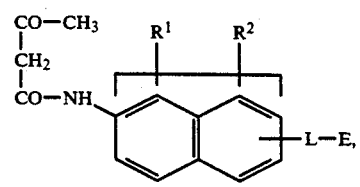 (XIXf)

where
$T^2$ is a benzene or naphthalene nucleus,
$R^{17}$ is methyl, carboxyl, methoxycarbonyl, ethoxycarbonyl or phenyl, $R^{18}$ is $C_1$–$C_4$-alkyl, benzyl, phenylethyl or phenyl, the phenyl nuclei being in each case unsubstituted or substituted by fluorine, chlorine, bromine, methyl, methoxy, cyano, hydroxysulfonyl, carboxyl, acetyl, nitro, carbamoyl or sulfamoyl, and L, $R^1$, $R^2$, $R^5$, $R^6$, $R^{12}$, $R^{13}$, $R^{15}$, $R^{16}$, p and E are each as defined above.

Pyrazolone coupling components which carry fiber-reactive radicals E are derived for example from the following pyrazolones: 1-(3'- or 4'-aminophenyl)-, 1-(2'-hydroxysulfonyl-5'-aminophenyl)-, 1-(2'-methoxy-5'-aminophenyl)-3-carboxypyrazole-5-one, 1-(3'- or 4'-aminophenyl)-, 1-(3'- or 4'-nitrophenyl)-3-methyl-pyrazol-5-one, 1-(3'- or 4'-nitrophenyl)-, 1-(6'-nitro-4',8'-dihydroxysulfonylnaphth-2'-yl)-or 1-(6'-amino-4',8'-dihydroxysulfonylnaphth-2'-yl)-or 1-(6'-amino-4',8'-dihydroxysulfonylnaphth-2'-yl)-3-carboxypyrazol-5-one.

Instead of azo dye radicals, the dyes of the formula I can also contain corresponding metal complex dye radicals. Suitable complexing metals are in particular copper, cobalt, chromium, nickel and iron, of which copper, cobalt and chromium are preferred.

In the metal complex dye radicals, the metallized groups are each preferably disposed ortho to the azo group, for example in the form of o,o'-dihydroxy-, o-hydroxy-o'-carboxy, o-carboxy-o'-amino- or o-hydroxy-o'-amino-azo groups.

X in the formula I is further for example the radical of a copper formazan dye. Copper formazans are known per se and described for example in K. Venkataraman The Chemistry of Synthetic Dyes, vol. III, Academic Press, New York, London, 1970.

Particular preference is given to copper formazan dyes of the formula XX

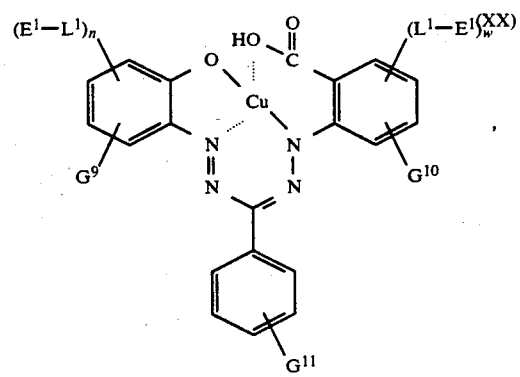

where
$G^9$, $G^{10}$ and $G^{11}$ are identical or different and each is independently of the others hydrogen or hydroxysulfonyl,
n is 0 or 1,
w is 0 or 1 and $E^1$ and $L^1$ are each as defined above, with the proviso that n and w are not both 0.

A method for preparing the formazans underlying these dyes is described for example in earlier Patent Application DE-A-3,737,536.

X in the formula I is further for example the radical of an anthraquinone dye. Anthraquinones are known per se and described for example in K. Venkataraman, The Chemistry of Synthetic Dyes, vol. II, Academic Press, New York, 1952.

Particular preference is given to anthraquinone dyes of the formula XXI

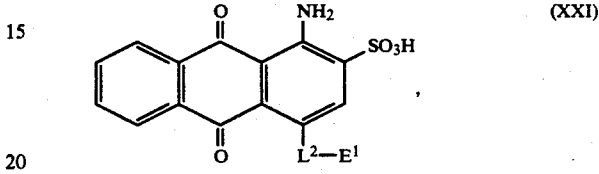

where
$L^2$ is the radical

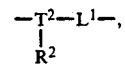

where $L^1$, $R^2$ and $T^2$ are each as defined above, or in particular the radical —NH—, and $E^1$ is as defined above.

X in the formula I is further for example the radical of a triphendioxazine dye. Triphendioxazines are known per se and described for example in EP-A-141,359 and earlier Patent Application DE-A-3,735,057.

Particular preference is given to triphendioxazine dyes of the formula XXII

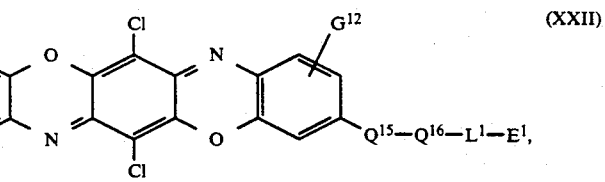

where
$E^1$ and $L^1$ are each as defined above,
$G^{12}$ is hydroxysulfonyl or the radical $SO_2$—$C_2H_4$—$OSO_3H$,
$Q^{15}$ is hydrogen, imino or $C_1$–$C_4$-alkylimino and
$Q^{16}$ is straight-chain or branched $C_2$–$C_4$-alkylene or phenylene.

X in the formula I is further for example the radical of a metallized phthalocyanine dye. Phthalocyanines are known per se and described for example in F. H. Moser, D. L. Thomas, The Phthalocyanines, vol. II, CRC Press, Boca Raton, Fla. 1983.

Particular preference is given to phthalocyanine dyes of the formula XXIII

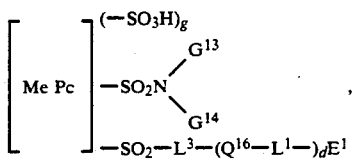 (XXIII)

where
$G^{13}$ and $G^{14}$ are identical or different and each is independently of the other hydrogen or $C_1$-$C_4$-alkyl,
$L^3$ is imino or $C_1$-$C_4$-alkylimino,
g is 0, 1, 2 or 3,
d is 0 or 1, and $L^1$, E and $Q^{16}$ are each as defined above.

The present invention further provides novel benzyl compounds of the formula III

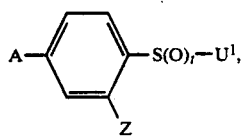 (III)

where
A is nitro or amino,
$U^1$ is $C_1$-$C_4$-alkyl, phenyl, $C_2$-$C_{10}$-alkenyl or the radical

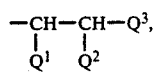

where $Q^1$ and $Q^2$ are identical or different and each is independently of the other hydrogen or $C_1$-$C_4$-alkyl and $Q^3$ is hydroxyl or a group which is detachable under alkaline reaction conditions,
Z is the radical

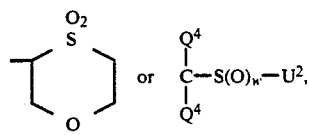

where each $Q^4$ is independently of the other hydrogen or $C_1$-$C_4$-alkyl which may be substituted by cyano, $U^2$ is $C_1$-$C_4$-alkyl, phenyl, $C_2$-$C_{10}$-alkenyl or the radical

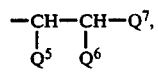

where $Q^5$ and $Q^6$ are identical or different and each is independently of the other hydrogen or $C_1$-$C_4$-alkyl, $Q^7$ is hydroxyl or a group which is detachable under alkaline reaction conditions, w is 0, 1 or 2, and
t is 0, 1 or 2, with the proviso that at least one of the two radicals $U^1$ and $U^2$ is not $C_1$-$C_4$-alkyl or phenyl.

Examples of $Q^1$, $Q^2$, $Q^3$, $Q^4$, $Q^5$, $Q^6$ and $Q^7$ were given above.

The novel benzyl compounds, which are useful intermediates for the synthesis of the novel double attachment reactive dyes, can be obtained in a conventional manner as described for example in earlier Patent Application DE-A-3,731,202.

For example, it is possible to react a compound of the formula XXIV

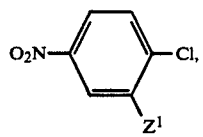 (XXIV)

where $Z^1$ has the meanings of Z, except $C_2$-$C_{10}$-alkenyl, with a thioalkanol, for example 2-thiethanol, 2-methyl-2-thioethanol or 1-methyl-2-thioethanol.

By reduction of the nitro to an amino group with or without oxidation of the sulfur atom to sulfoxide or sulfone, in either order, and subsequent esterification, for example with chlorosulfonic acid, it is possible to arrive at the benzyl sulfone of the formula XXV

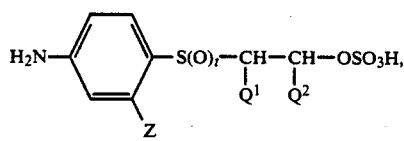 (XXV)

where $Q^1$, $Q^2$, Z and t are each as defined above.

Compounds of the formula XXIV can be obtained for example by reacting a benzyl chloride of the formula XXVI

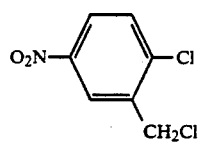 (XXVI)

with a thioalkanol, optionally oxidizing the resulting thioether, and subsequently esterifying it, for example with chlorosulfonic acid.

Starting from benzyl chloride XXVI it is for example also possible, by the abovementioned methods, to replace in a single step not only the chlorine atom in the aromatic ring by the radical —S(O)$_t$—U$^1$ but also the chlorine atom of the benzyl group by the radical —S-(O)$_w$—U$^2$, in which case the radicals —S(O)$_t$—U$^1$ and —S(O)$_w$—U$^2$ are identical and U$^1$, U$^2$, t and w are each as defined above.

In place of the sulfuric ester it is also possible to introduce the other radicals which are detachable under alkaline reaction conditions in a conventional manner.

The reactive dyes of the formula I are prepared for example by reacting a suitable organic dye or a suitable dye intermediate and the fiber-reactive compound of the formula XXVII

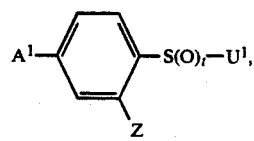 (XXVII)

where Z, $U^1$ and t are each as defined above and $A^1$ is the radical

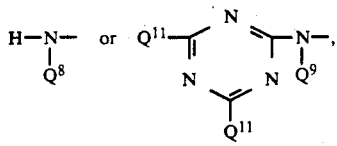

where $Q^8$, $Q^9$ and $Q^{11}$ are each as defined above, and, if dye intermediates have been used, converting the resulting intermediate compounds into the desired dyes in a conventional manner.

If the compound X-H is a coupling component, it is possible to obtain the dyes according to the invention for example by diazotizing the fiber-reactive double attachment system of the formula XXVIII

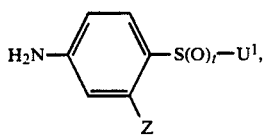

(XXVIII)

where Z, $U^1$ and t are each as defined above, and coupling the diazonium product with the coupling component X-H in a conventional manner.

The double attachment reactive dyes according to the invention are advantageously suitable for dyeing hydroxyl-containing fibers, in particular cotton, but also wool.

Suitable dyeing methods are the known reactive dyeing methods, in particular exhaust methods at from 40° to 80° C. and cold pad-batch methods. The novel dyes are notable for high yield and high wet fastness.

The Examples which follow illustrate the invention in more detail. Percentages are by weight, unless otherwise stated.

In the table examples, the abbreviations E-1 to E-8 have the following meanings:

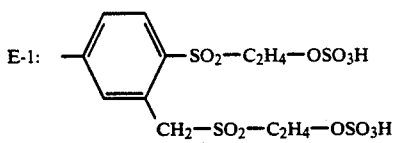

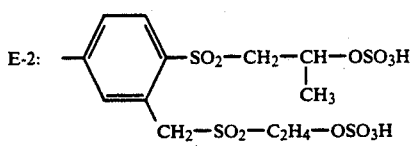

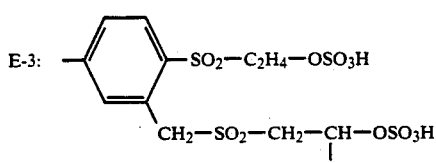

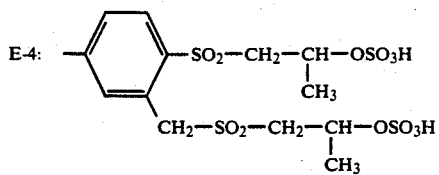

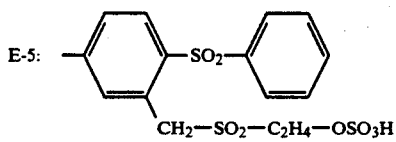

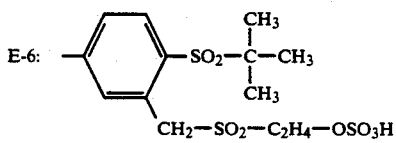

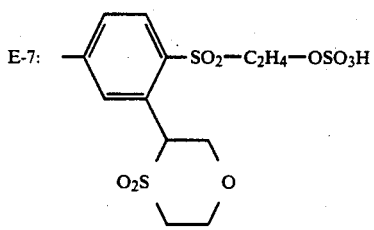

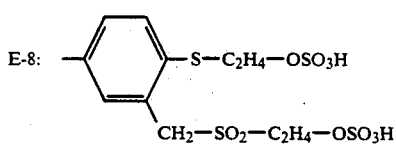

EXAMPLE 1

A solution of 24.2 g of 4-(2'-sulfatoethyl)-3-(2''-sulfatoethylsulfonylmethyl)aniline in 270 ml of water was diazotized with 30 ml of 5N hydrochloric acid and 15 ml of 3.33N $NaNO_2$ solution at from 0° to 5° C. and admixed with a neutral aqueous solution of 14.2 g of 1-(4-sulfophenyl)-3-carboxy-5-pyrazolone. Sodium bicarbonate was sprinkled in to maintain a pH of from 5 to 6. After the coupling had ended, the dye was salted out with potassium chloride and gently dried under reduced pressure. It dyes cotton in light-fast yellow shades and conforms to the formula

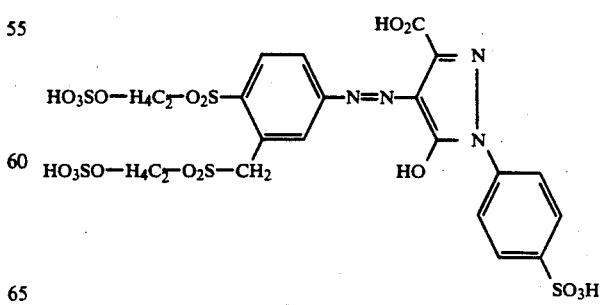

Further dyes according to the invention, which were obtaine din a similar manner, are given in Table 1:

TABLE 1

E—N=N—K

| Example No. | E | K | Hue on cotton |
|---|---|---|---|
| 2 | E-1 | 3-methyl-5-(CH₂SO₃H)-6-hydroxy-1-ethyl-4-oxo-pyridone structure with CH₃, CH₂SO₃H, OH, =O, N-C₂H₅ | greenish yellow |
| 3 | E-1 | pyridone with CH₃, CONH₂, OH, =O, N-C₂H₅ | greenish yellow |
| 4 | E-1 | pyridone with CH₃, OH, =O, N-CH₃ | greenish yellow |
| 5 | E-5 | pyrazolone (H₃C, CH₃, HO) coupled to 2-methyl-4-sulfophenyl | yellow |
| 6 | E-7 | pyrazolone (HO₂C, CH₃, HO) coupled to 4-sulfophenyl | yellow |
| 7 | E-1 | naphthalene with HO, HO₃S, SO₃H substituents | orange |
| 8 | E-2 | naphthalene with HO, HO₃S, SO₃H substituents | orange |
| 9 | E-3 | naphthalene with HO, HO₃S, SO₃H substituents | orange |
| 10 | E-4 | naphthalene with HO, HO₃S, SO₃H substituents | orange |

TABLE 1-continued

E—N=N—K

| Example No. | E | K | Hue on cotton |
|---|---|---|---|
| 11 | E-1 | 8-hydroxy-3-methyl-naphthalene-1,5-disulfonic acid (HO, SO₃H, CH₃, SO₃H on naphthalene) | orange |
| 12 | E-2 | 8-hydroxy-7-methyl-naphthalene-1,6-disulfonic acid (HO, SO₃H, CH₃, HO₃S on naphthalene) | orange |
| 13 | E-1 | 4-hydroxy-3-methyl-naphthalene-1-sulfonic acid | reddish orange |
| 14 | E-2 | 4-hydroxy-3-methyl-naphthalene-1-sulfonic acid | reddish orange |
| 15 | E-1 | 4,6-dihydroxy-2-hydroxy-5-methylpyrimidine | greenish yellow |
| 16 | E-1 | 4-amino-6-hydroxy-5-methyl-2-morpholinopyrimidine | yellow |
| 17 | E-1 | 2,6-dihydroxy-3-methyl-isonicotinic acid (CO₂H, CH₃, HO, N, OH) | greenish yellow |
| 18 | E-1 | 6-amino-5-methyl-naphthalene-1,3-disulfonic acid (H₂N, CH₃, SO₃H, HO₃S on naphthalene) | reddish orange |

EXAMPLE 19

13 g of 4-(2'-hydroxyethylsulfonyl)-3-(2''-hydroxyethylsulfonylmethyl)aniline were dissolved in p200 ml of water at 60° C., admixed with 13.5 ml of 3.33 N NaNO₂ solution, and added to a mixture of 400 g of ice and 30 ml of 5 NHCl in the course of 30 minutes. After the diazotization had ended, the resulting solution was added in the course of one hour to a solution of 15.5 g suction, and the residue was gently dried under reduced pressure. The dye obtained conforms to the formula

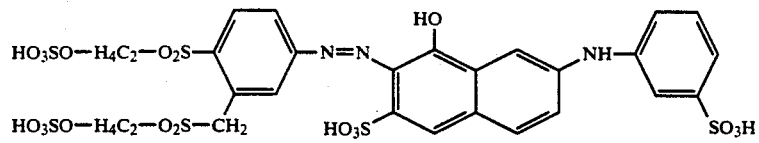

of 1-hydroxy-7-(3'-sulfophenylamino)naphthalene-3-sulfonic acid in 200 ml of aqueous sodium hydroxide solution while a pH of from 8 to 8.5 was maintained by the simultaneous addition of 50 ml of sodium carbonate solution. The resulting solution was evaporated down, and the residue was dried at 60° C. under reduced pressure. The residue was suspended in 200 ml of anhydrous N-methylpyrrolidone, and 19 g of chlorosulfonic acid were added dropwise. After stirring at 50° C. for 11 hours the mixture was discharged onto ice, the resulting mixture was brought to pH 6 with sodium bicarbonate, and precipitated sodium sulfate was filtered off with suction at from 0° to 5° C. The filtrate was evaporated, 1-propanol was added, the mixture was filtered off with and dyes cotton in fast brown shades.

EXAMPLE 20

24.9 g of 4-(sulfatoethylsulfonyl)-3-(2''-sulfatopropyl-sulfonylmethyl)aniline in 480 ml of water were diazotized in the presence of hydrochloric acid at from 0° to 5° C. and admixed with a neutral aqueous solution of 21.2 g of 1-benzoylamino-8-hydroxynaphthalene-4,6-disulfonic acid. The coupling was completed at pH 5-6 by sprinkling in sodium bicarbonate, and the dye formed was salted out with potassium chloride and gently dried under reduced pressure. It dyes cotton in brilliant red shades having good fastness properties and conforms to the formula

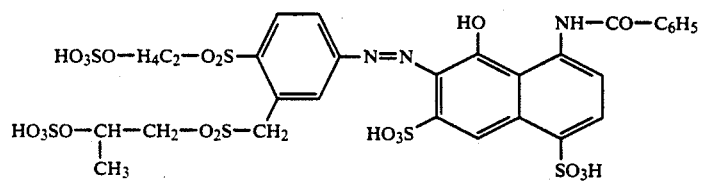

Further dyes according to the invention are given in Table 2.

TABLE 2

E—N=N—K

| Example No. | E | K | Hue on cotton |
|---|---|---|---|
| 21 | E-1 | HO / NH—COCH$_3$ naphthalene with HO$_3$S and SO$_3$H | red |
| 22 | E-2 | HO / NH—COCH$_3$ naphthalene with HO$_3$S and SO$_3$H | red |
| 23 | E-3 | HO / NH—COCH$_3$ naphthalene with HO$_3$S and SO$_3$H | red |
| 24 | E-5 | HO / NH—COC$_6$H$_5$ naphthalene with HO$_3$S and SO$_3$H | red |

TABLE 2-continued

E—N=N—K

| Example No. | E | K | Hue on cotton |
|---|---|---|---|
| 25 | E-8 | 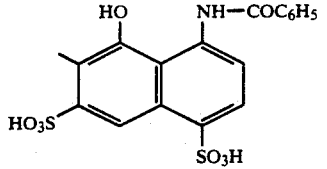 4-benzoylamino-5-hydroxy-6-methyl-naphthalene-2-sulfonic acid (with extra SO3H) | bluish red |
| 26 | E-1 | 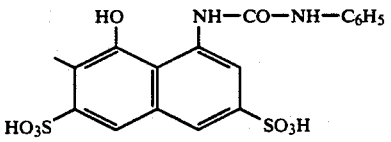 phenylureido-hydroxy-methyl-naphthalenedisulfonic acid | bluish red |
| 27 | E-1 | 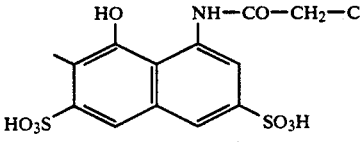 NH—CO—CH2—Cl | red |
| 28 | E-1 | 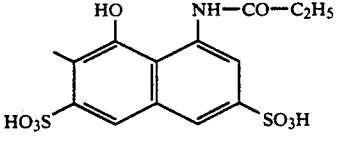 NH—CO—C2H5 | red |
| 29 | E-1 | 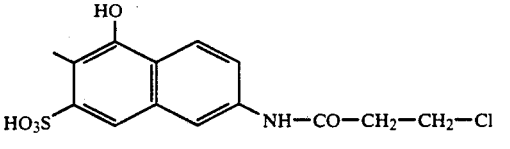 NH—CO—CH2—CH2—Cl | orange |
| 30 | E-2 | 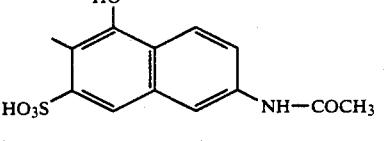 NH—COCH3 | orange |
| 31 | E-1 | 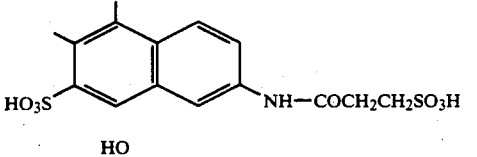 NH—COCH2CH2SO3H | orange |
| 32 | E-1 | 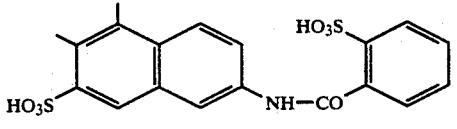 | orange |
| 33 | E-1 | 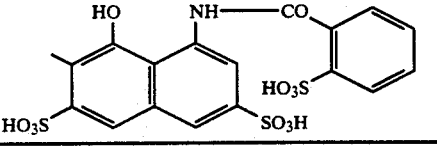 | red |

EXAMPLE 34

8.4 g of 4-(2'-sulfatoethylsulfonyl)-3-(2''-sulfatoethylsulfonylmethyl)aniline were dissolved in 200 ml of H$_2$O at pH 6 with NaHCO$_3$ and diazotized at 0° C. with 3.2 ml of 5N NaNO$_2$ solution, 2 ml of formic acid and 3 ml of 10N HCl. To this solution was added dropwise a suspension of 5.6 g of 1-amino-8-hydroxynaphthalene-3,6-disulfonic acid in 100 ml of H$_2$O at pH 1. Stirring was continued for 4 hours, the mixture was cooled down to 10° C., and 8.4 g of 4-(2'-sulfatoethylsulfonyl)-3-(2'-sulfatoethylsulfonylmethyl)aniline (diazotized as described above) were added dropwise, and coupling was effected at pH 4–4.5 using sodium bicarbonate. Stirring was continued overnight, and the dye was salted out with KCl and gently dried. It has the formula This was followed by the dropwise addition at 10° C. of a diazonium salt solution prepared as follows: 21 g of 4-(2'-sulfatoethylsulfonyl)-3-(2''-sulfatoethylsulfonylmethyl)aniline (Na salt), dissolved in 200 ml of cold H₂O at pH 6 with sodium bicarbonate, were diazotized

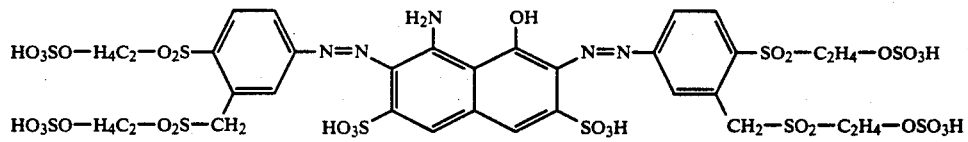

and dyes cotton in navy shades having good fastness properties.

EXAMPLE 35

7 g of sulfanilamide were dissolved in 200 ml of H₂O and diazotized at 0° C. with 8 ml of 5N sodium nitrite solution and 10 ml of 10N hydrochloric acid in the course of 1 hour. A suspension of 13.7 g of 1-amino-8-hydroxynaphthalene-3,6-disulfonic acid (Na salt) in 100 ml of water was added dropwise. The pH was 2.5. Stirring was continued overnight at room temperature.

with 8 ml of 5N sodium nitrite solution, 5 ml of formic acid and 7 ml of 10N hydrochloric acid at from 0° to 5° C. for 1 hour.

The pH was maintained at 4.5–5 with sodium bicarbonate for 2 hours, and potassium chloride was added for salting out. The precipitate was filtered off with suction and dried, leaving a black powder which dyes cotton in navy shades of good light fastness. The dye conforms to the formula

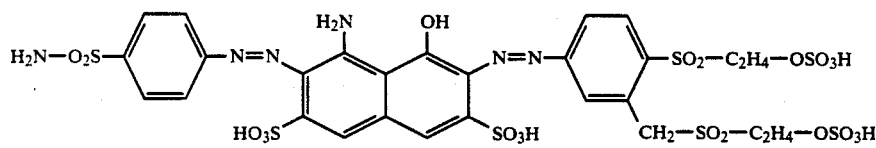

Further dyes according to the invention are given in Table 3.

TABLE 3

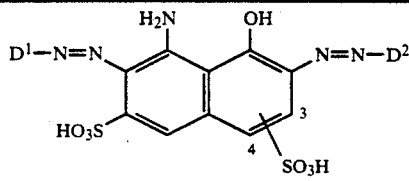

| Example No. | D¹ | D² | Position 3 or 4 | Hue on cotton |
|---|---|---|---|---|
| 36 | HO₃S—⟨phenyl⟩— | E-2 | 3 | navy |
| 37 | H₂NO₂S—⟨phenyl⟩— | E-2 | 3 | navy |
| 38 | ⟨phenyl with SO₃ and HO₃S⟩ | E-5 | 3 | navy |
| 39 | ⟨naphthyl with SO₃H, SO₃H⟩ | E-1 | 3 | navy |

TABLE 3-continued (Structure: naphthalene core with H₂N, OH, two azo groups D¹—N=N— and —N=N—D², HO₃S at one position, SO₃H at position 3 or 4)

| Example No. | D¹ | D² | Position 3 or 4 | Hue on cotton |
|---|---|---|---|---|
| 40 | E-2 | E-2 | 3 | navy |
| 41 | E-3 | E-3 | 3 | navy |
| 42 | E-1 | (4-sulfo-3-methylphenyl)amino-chloro-triazinyl-(3-sulfophenyl)amino | 3 | navy |
| 43 | E-1 | (4-sulfo-3-methylphenyl)amino-2,5,6-trichloropyrimidin-4-yl | 3 | navy |
| 44 | E-2 | (4-sulfo-3-methylphenyl)amino-fluoro-triazinyl-(3-sulfophenyl)amino | 3 | navy |
| 45 | E-1 | 4-sulfophenyl | 3 | navy |
| 46 | E-1 | 7-methyl-1,5-disulfonaphthyl | 4 | navy |

TABLE 3-continued

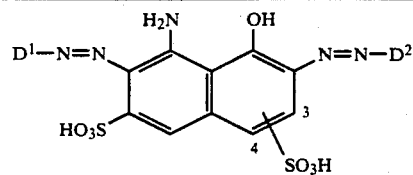

| Example No. | $D^1$ | $D^2$ | Position 3 or 4 | Hue on cotton |
|---|---|---|---|---|
| 47 | E-1 | 4-CH₃-C₆H₄-SO₂-CH₂-CH=CH₂ | 3 | navy |
| 48 | E-2 | 4-CH₃-C₆H₄-SO₂-C₂H₄-OSO₃H | 3 | navy |
| 49 | E-1 | (3-methylphenyl)-substituted dichloropyrimidine | 3 | navy |
| 50 | E-2 | sulfo/methylphenyl-NH-(chloro-difluoro-pyrimidinyl) | 3 | navy |
| 51 | E-1 | sulfo/methylphenyl-NH-CO-phenyl-(dichloropyridazinonyl) | 3 | navy |
| 52 | 4-chloro-2-methyl-5-sulfo-benzenesulfonic acid (HO₃S, SO₃H, Cl, CH₃) | E-5 | 3 | reddish navy |
| 53 | E-1 | E-1 | 4 | navy |
| 54 | E-2 | E-2 | 4 | navy |

TABLE 3-continued

Structure:

D¹—N=N— attached to naphthalene bearing H₂N, OH, with second —N=N—D² group; HO₃S on one ring and SO₃H at position 3 or 4.

| Example No. | D¹ | D² | Position 3 or 4 | Hue on cotton |
|---|---|---|---|---|
| 55 | CH₂=CH—CH₂O₂S—C₆H₄— | E-1 | 3 | navy |
| 56 | HO₃SOH₄C₂O₂S—C₆H₄— | E-1 | 3 | navy |
| 57 | o-(SO₃H)C₆H₄— | E-1 | 3 | navy |
| 58 | HO₃SOH₄C₂HNO₂S—C₆H₄— | E-1 | 3 | navy |
| 59 | E-1 | —C₆H₄—SO₂NHC₂H₄OSO₃H | 3 | navy |
| 60 | E-5 | E-1 | 3 | navy |
| 61 | E-2 | 4-(HO₃S)-3-methylphenyl-NH-(4,6-dichloro-1,3,5-triazin-2-yl) | 3 | navy |
| 62 | 4-methyl-2,5-disulfo-phenyl (HO₃S, SO₃H, CH₃ substituted benzene) | E-6 | 3 | navy |
| 63 | E-6 | 4-methyl-2,5-disulfo-phenyl (H₃C, SO₃H, HO₃S substituted benzene) | 3 | navy |

TABLE 3-continued

Structure:

$$D^1-N=N-\underset{HO_3S}{\underset{|}{\text{naphthalene}}}\text{(8-NH}_2\text{, 1-OH, 6-SO}_3\text{H, 4-SO}_3\text{H at 3 or 4)}-N=N-D^2$$

with H₂N at position 8, OH at position 1, HO₃S at position 6, and SO₃H at position 3 or 4.

| Example No. | D¹ | D² | Position 3 or 4 | Hue on cotton |
|---|---|---|---|---|
| 64 | 2-sulfo-5-methylphenyl (SO₃H, H₃C-) | E-1 | 3 | navy |
| 65 | E-1 | 2-sulfo-5-methylphenyl (HO₃S, CH₃) | 3 | navy |
| 66 | 3-chloro-4-sulfophenyl (Cl, HO₃S-) | E-1 | 3 | navy |
| 67 | E-3 | 3-chloro-4-sulfophenyl (Cl, -SO₃H) | 3 | navy |
| 68 | 2-sulfophenyl (SO₃H) | E-1 | 4 | navy |
| 69 | 2-sulfo-5-methylphenyl (SO₃H, H₃C-) | E-1 | 4 | navy |
| 70 | 3-chloro-4-sulfophenyl (Cl, HO₃S-) | E-1 | 4 | navy |

EXAMPLE 71

24.2 g of 4-(2'-sulfatoethylsulfonyl)-5-(2"-sulfatoethylsulfonylmethyl)aniline which had been diazotized in the presence of hydrochloric acid, in 300 ml of water, were added at from 0° to 5° C. to a neutral solution in 800 ml of water of 25.4 g of the secondary condensation product of aniline-3-sulfonic acid, 2,4,6-trifluoro-1,3,5-triazine and 2-amino-5-hydroxynaphthalene-7-sulfonic acid. Sodium bicarbonate was added to bring about a pH of 5–6, and the resulting dye was salted out with sodium chloride. Gentle drying left a reddish orange powder which dyes cotton in brilliant orange shades. The dye conforms to the formula

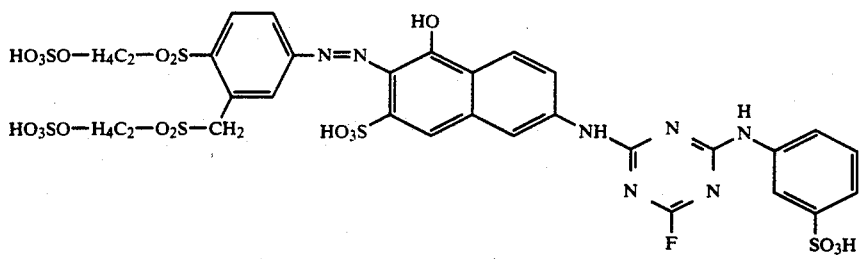

EXAMPLE 72

24.9 parts of 4-(2'-sulfatoethylsulfonyl)-3-(2"-sulfatopropylsulfonylmethyl)aniline which had been diazotized in the presence of hydrochloric acid, in 300 ml of water, were added to a neutral solution of 30.2 g of the secondary condensation product of 1-amino-8-hydroxynaphthalene-3,6-disulfonic acid, cyanuric chloride and aniline-4-sulfonic acid in 700 ml of water. Sodium bicarbonate was added to complete the coupling at pH 5-6. The dye formed was salted out with sodium chloride and gently dried. It conforms to the formula

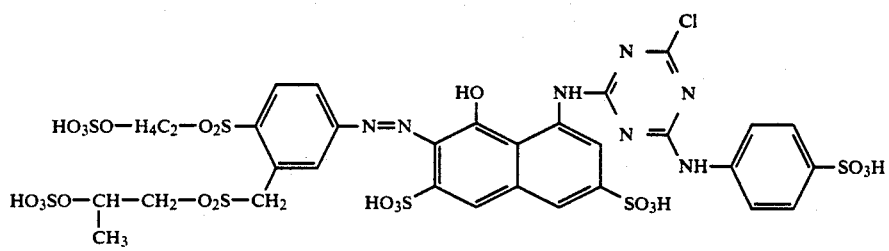

and dyes cotton in brilliant red shades having good fastness properties.

The method of Examples 71 and 72 was also used to prepare the dyes listed in Table 4.

TABLE 4

E—N=N—K (triazine with X and R substituents)

| Ex. No. | E | K | X | R | Hue on cotton |
|---|---|---|---|---|---|
| 73 | E-2 | (OH, NH— naphthalene with HO3S and SO3H) | Cl | OCH3 | red |
| 74 | E-2 | (OH, NH— naphthalene with HO3S and SO3H) | F | NH—phenyl-SO3H | red |
| 75 | E-1 | (OH, NH— naphthalene with HO3S and SO3H) | Cl | OCH2CH2OCH3 | red |
| 76 | E-1 | (OH, NH— naphthalene with HO3S and NH—) | Cl | NH—phenyl-SO3H | orange |

TABLE 4-continued $$E-N=N-K \quad \begin{array}{c} N \\ \diagup \diagdown \\ N \quad N \\ \diagdown \diagup \\ R \end{array} X$$

| Ex. No. | E | K | X | R | Hue on cotton |
|---|---|---|---|---|---|
| 77 | E-1 | HO₂C-[pyrazolone with N=N to phenyl(SO₃H)(NH-)]-OH, CH₃ | Cl | NH-phenyl-SO₃H | yellow |
| 78 | E-2 | HO₂C-[pyrazolone with N=N to phenyl(NH-)]-OH, CH₃ | Cl | NH-phenyl-SO₃H | yellow |
| 79 | E-1 | HO₂C-[pyrazolone with N=N to phenyl(NH-)]-OH, CH₃ | F | NH-phenyl-SO₃H | yellow |
| 80 | E-1 | [pyridone: CH₃, CONH₂, CH₃, HO, N-CH₂-CH₂-CH₂-NH-, =O] | Cl | NH-phenyl-SO₃H | greenish yellow |

EXAMPLE 81

A neutral aqueous solution of 24.2 g of 4-(2'-sulfatoethylsulfonyl)-3-(2''-sulfatoethylsulfonylmethyl)-aniline in 650 ml of water was admixed with a suspension of 9.5 g of cyanuric chloride in 150 ml of ice water by stirring at from 0° to 5° C. for 1 hour during which a pH of from 5-6 was maintained by addition of sodium bicarbonate. After filtration, the filtrate was added to a solution of 9.5 g of 1,3-diaminobenzene-4-sulfonic acid in 100 ml of water stirred at 40° C. and pH 5-6, and the resulting mixture was maintained at from 0° to 5° C. and pH 5-6 for 2 hours.

After the reaction had ended, the diazonium salt was formed at from 0° to 5° C. by addition of 15 ml of 3.33N NaNO₂ and 30 ml of 5N hydrochloric acid and coupled onto 11.1 g of 1,4-dimethyl-3-sulfomethyl-6-hydroxy-2-pyridone. The dye obtained was salted out with sodium chloride and gently dried under reduced pressure. It dyes cotton in brilliant fast greenish yellow shades and conforms to the formula

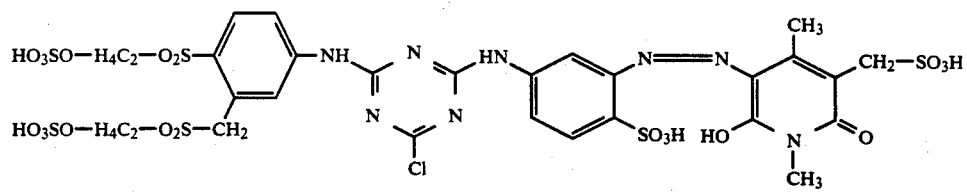

EXAMPLE 82

33 g of the sodium salt of the dye of the formula

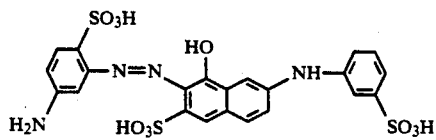

were dissolved in water at pH 6 and 40° C. and admixed with 31.6 g of the condensation product of cyanuric chloride and 4-(2'-sulfatoethylsulfonyl)-3-(2''-sulfatoethylsulfonylmethyl)aniline described in Example 81 and dissolved in 800 ml of water, by stirring at 40° C. for a further 2 hours during which a pH of from 5–6 is maintained by sprinkling in sodium bicarbonate. The dye, precipitated with potassium chloride and gently dried, gives brown dyeings on cotton and conforms to the formula

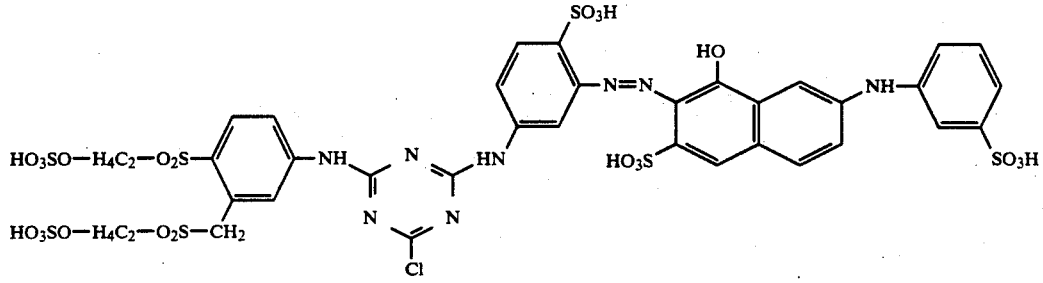

The same method was used to obtain the dyes described in Table 5.

TABLE 5

| Ex. No. | E | X | D | K | Hue on cotton |
|---|---|---|---|---|---|
| 83 | E-1 | Cl | phenyl-SO₃H | HO, NH—COC₆H₅, HO₃S, SO₃H naphthyl | red |
| 84 | E-2 | F | phenyl-SO₃H | HO, NH—COC₆H₅, HO₃S, SO₃H naphthyl | red |
| 85 | E-3 | F | phenyl-SO₃H | HO, NH—COC₆H₅, HO₃S, SO₃H naphthyl | red |
| 86 | E-1 | Cl | phenyl-SO₃H | HO, NH—COCH₃, HO₃S, SO₃H naphthyl | red |
| 87 | E-1 | Cl | phenyl-SO₃H | HO, NH—COC₂H₅, HO₃S, SO₃H naphthyl | red |

TABLE 5-continued
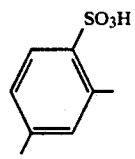
| Ex. No. | E | X | D | K | Hue on cotton |
|---|---|---|---|---|---|
| 88 | E-2 | Cl | 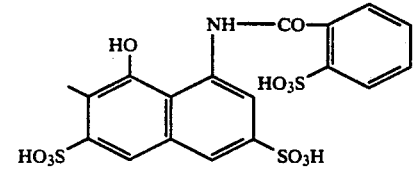 | 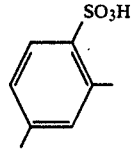 | red |
| 89 | E-1 | Cl | 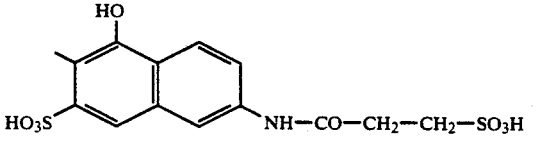 | 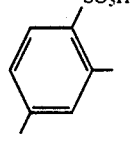 | orange |
| 90 | E-1 | Cl | 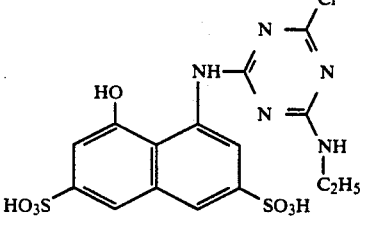 | 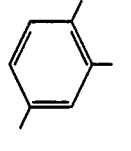 | red |
| 91 | E-1 | Cl | 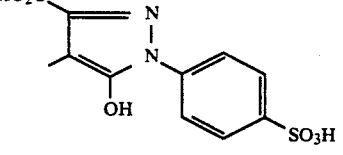 | 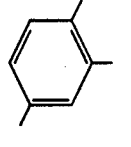 | yellow |
| 92 | E-1 | Cl | 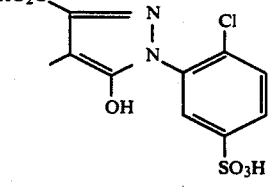 | 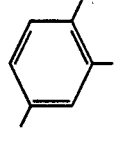 | yellow |
| 93 | E-1 | Cl | 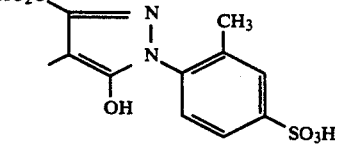 | 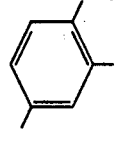 | yellow |
| 94 | E-1 | Cl | 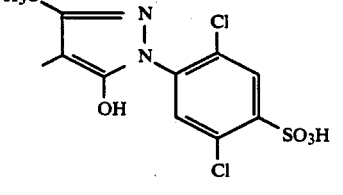 |  | yellow |

TABLE 5-continued

Structure:
$$\text{E-NH}-\underset{\underset{\text{NH}}{|}}{\text{C}}(\text{=N})-\text{N=C}(\text{X})-\text{N=C}-\text{NH}-\text{D}-\text{N=N}-\text{K}$$
(triazine with X, E—NH, and NH—D—N=N—K substituents)

| Ex. No. | E | X | D | K | Hue on cotton |
|---|---|---|---|---|---|
| 95 | E-5 | Cl | 2,4-disubstituted benzene with SO₃H | 1-(2,5-disulfophenyl)-3-methyl-5-hydroxypyrazole azo | yellow |
| 96 | E-1 | Cl | 2,4-disubstituted benzene with SO₃H | 1,4-dimethyl-3-methyl-6-hydroxy-2-pyridone | greenish yellow |
| 97 | E-1 | Cl | 2,4-disubstituted benzene with SO₃H | 1-ethyl-3-methyl-4-methyl-5-carbamoyl-6-hydroxy-2-pyridone | greenish yellow |
| 98 | E-1 | Cl | 2,4-disubstituted benzene with SO₃H | 1-ethyl-3-methyl-4-methyl-5-(CH₂SO₃H)-6-hydroxy-2-pyridone | greenish yellow |
| 99 | E-1 | Cl | 2,4-disubstituted benzene with SO₃H | 3-methyl-4-carboxy-2,6-dihydroxypyridine | greenish yellow |
| 100 | E-1 | Cl | 2,4-disubstituted benzene with SO₃H | 2-methyl-1-hydroxy-4-sulfonaphthalene | reddish orange |
| 101 | E-1 | Cl | 2,4-disubstituted benzene with SO₃H | 2-methyl-1-hydroxy-3,6-disulfonaphthalene | orange |
| 102 | E-1 | Cl | 2,4-disubstituted benzene with SO₃H | 2-methyl-1-hydroxy-6-sulfo-8-sulfonaphthalene | orange |

TABLE 5-continued
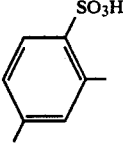
| Ex. No. | E | X | D | K | Hue on cotton |
|---|---|---|---|---|---|
| 103 | E-1 | Cl | 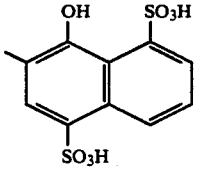 | 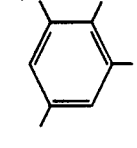 | reddish orange |
| 104 | E-1 | Cl | 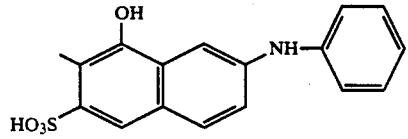 | 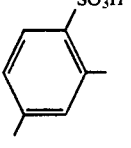 | brown |
| 105 | E-1 | Cl | 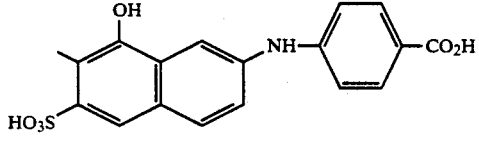 | 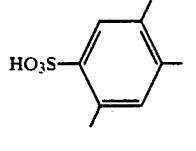 | brown |
| 106 | E-1 | Cl | 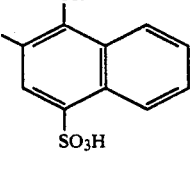 | 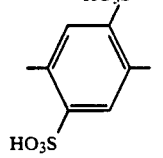 | reddish orange |
| 107 | E-1 | Cl | 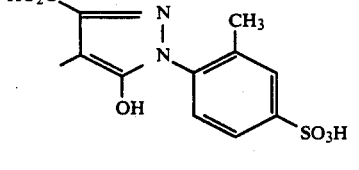 | 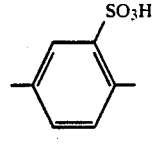 | reddish yellow |
| 108 | E-1 | Cl | 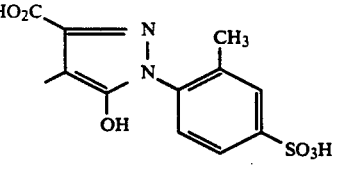 | 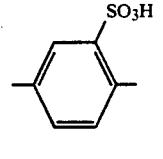 | reddish yellow |
| 109 | E-1 | Cl | 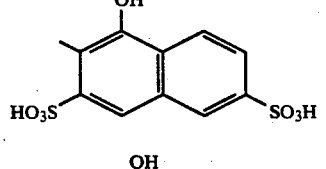 | 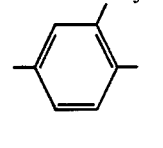 | red |
| 110 | E-1 | Cl | 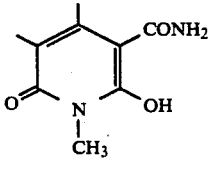 | | reddish yellow |

TABLE 5-continued

General structure:

$$\begin{array}{c} X \\ | \\ \text{(triazine ring with substituents)} \end{array} \text{—NH—D—N=N—K}$$

with E—NH on the triazine.

| Ex. No. | E | X | D | K | Hue on cotton |
|---|---|---|---|---|---|
| 111 | E-1 | Cl | 2,5-disubstituted benzene with SO₃H | 3-methyl-2,6-dihydroxypyridine-4-carboxylic acid (CO₂H) | reddish yellow |
| 112 | E-1 | Cl | benzene-SO₃H | 4-hydroxy-3-methyl-7-acetamido-naphthalene-2-sulfonic acid (HO₃S, NH—COCH₃) | orange |
| 113 | E-1 | F | benzene-SO₃H | 4-hydroxy-3-methyl-7-acetamido-naphthalene-2-sulfonic acid | orange |
| 114 | E-1 | Cl | benzene-SO₃H | 8-hydroxy-7-methyl-2-acetamido-naphthalene-6-sulfonic acid | orange |
| 115 | E-1 | Cl | benzene-SO₃H | 4-hydroxy-3-methyl-6-amino-7-(3-chloropropionylamino)naphthalene (H₂N, NH—CO—CH₂—CH₂—Cl) | orange |
| 116 | E-1 | Cl | benzene-SO₃H | 4-hydroxy-3-methyl-7-acetamido-naphthalene-2-sulfonic acid | red |
| 117 | E-2 | Cl | benzene-1,4-disulfonic acid (SO₃H, HO₃S) | 4-hydroxy-3-methyl-7-acetamido-naphthalene-2-sulfonic acid | red |
| 118 | E-1 | Cl | benzene-SO₃H | 1,4-dimethyl-3-sulfo-6-hydroxy-N-methyl-2-pyridone (CH₃, SO₃H, HO, N—CH₃, =O) | greenish yellow |

TABLE 5-continued

Structure:
$$\text{E-NH-}\underset{\underset{\text{N}}{\|}}{\overset{\overset{\text{X}}{|}}{\text{C}}}\text{-NH-D-N=N-K}$$
(triazine with X, E-NH substituents, NH-D-N=N-K)

| Ex. No. | E | X | D | K | Hue on cotton |
|---|---|---|---|---|---|
| 119 | E-1 | Cl | naphthalene with two CH₃, SO₃H | naphthalene with OH, NH—COCH₃, CH₃, 2×SO₃H | bluish red |
| 120 | E-1 | Cl | benzene with SO₃H, HO₃S, 2×CH₃ | naphthalene with OH, CH₃, SO₃H | red |
| 121 | E-1 | Cl | benzene with SO₃H, 2×CH₃ | naphthalene with OH, SO₃H, HO₃S | red |
| 122 | E-1 | Cl | benzene with SO₃H, 2×CH₃ | naphthalene with OH, 2×SO₃H | red |

EXAMPLE 123

27.7 g of the aminoazo dye obtained by coupling diazotized 2-aminonaphthalene-3,6,8-trisulfonic acid onto 3-aminophenylurea were dissolved in 250 ml of water under neutral conditions and admixed at 40° C. with a neutral aqueous solution in 800 ml of water of 31.6 g of the condensation product of cyanuric chloride and 4-(2'-sulfatoethylsulfonyl)-3-(2"-sulfatoethylsulfonylmethyl)-aniline prepared as described in Example 81 by stirring for 2 hours during which a pH of 5–6 was maintained by sprinkling in sodium bicarbonate. As soon as there were no longer any free amino groups detectable by thin layer chromatography, potassium chloride was added for salting out, and the precipitate was gently dried under reduced pressure. The product conforms to the formula and dyes cotton in fast reddish yellow shades having good fastness properties.

EXAMPLE 124

The neutral aqueous solution of 31.6 g of the primary condensation product of cyanuric chloride and 4-(2'-sulfatoethylsulfonyl)-3-(2"-sulfatoethylsulfonylmethyl)aniline described in Example 81 was admixed with 15 g of 1-amino-8-hydroxynaphthalene-3,6-disulfonic acid by stirring at 40° C. for 2 hours during which a pH of 5–6 was maintained by addition of sodium bicarbonate. The mixture was ice-cooled to 0°–5° C., 8.7 g of diazotized aniline-2-sulfonic acid were added, and the coupling was completed at pH 5–6 by addition of sodium bicarbonate. The resulting dye has the structural formula

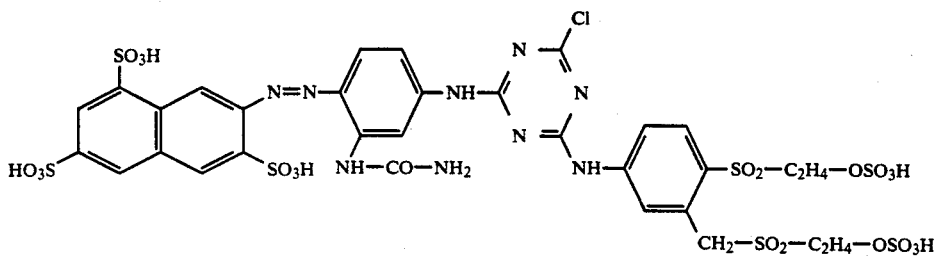

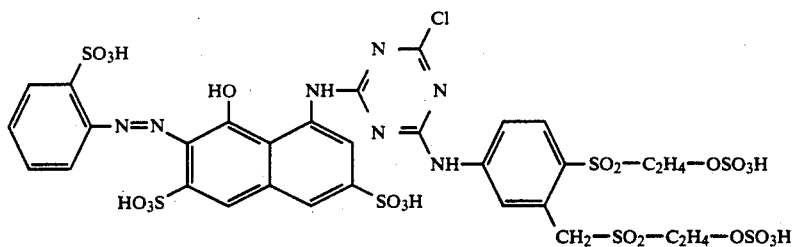

and dyes cotton in fast brilliant red shades.

The same method was used to obtain the dyes listed in Table 6.

TABLE 6

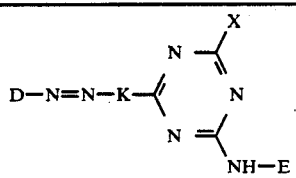

| Ex. No. | D | K | X | E | Hue on cotton |
|---|---|---|---|---|---|
| 125 | 2-sulfophenyl | 1-hydroxy-8-amino-3,6-disulfonaphthyl | Cl | E-1 | red |
| 126 | 2-sulfophenyl | 1-hydroxy-8-amino-3,6-disulfonaphthyl | F | E-2 | red |
| 127 | 4-methoxy-2-sulfophenyl | 1-hydroxy-8-amino-3,6-disulfonaphthyl | Cl | E-1 | dull bluish red |
| 128 | 4-methyl-2-sulfophenyl | 1-hydroxy-8-amino-3,6-disulfonaphthyl | Cl | E-1 | bluish red |
| 129 | 4-carboxyphenyl | 1-hydroxy-8-amino-3,6-disulfonaphthyl | Cl | E-1 | bluish red |
| 130 | 4-(allylsulfonyl)phenyl | 1-hydroxy-8-amino-3,6-disulfonaphthyl | Cl | E-1 | red |
| 131 | 4-(2-sulfatoethylsulfonyl)phenyl | 1-hydroxy-8-amino-3,6-disulfonaphthyl | Cl | E-1 | red |

TABLE 6-continued

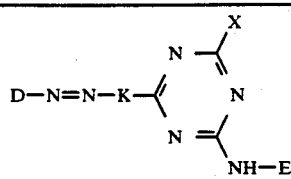

| Ex. No. | D | K | X | E | Hue on cotton |
|---|---|---|---|---|---|
| 132 | 2-methyl-naphthalene-1,5-disulfonic acid | 8-amino-1-hydroxy-naphthalene-3,6-disulfonic acid (2-methyl) | Cl | E-1 | bluish red |
| 133 | toluene | 8-amino-1-hydroxy-naphthalene (methyl, SO3H) | Cl | E-1 | red |
| 134 | 2-methylbenzenesulfonic acid | 6-amino-1-hydroxy-naphthalene-3-sulfonic acid (2-methyl) | Cl | E-1 | orange |
| 135 | 4-methoxy-2-methylbenzenesulfonic acid | 6-amino-1-hydroxy-naphthalene-3-sulfonic acid (2-methyl) | Cl | E-1 | orange |
| 136 | 5-methylbenzene-1,3-disulfonic acid | 6-amino-1-hydroxy-naphthalene-3-sulfonic acid (2-methyl) | Cl | E-1 | orange |
| 137 | 5-methoxy-2-methylbenzene-1,4-disulfonic acid | 6-amino-1-hydroxy-naphthalene-3-sulfonic acid (2-methyl) | Cl | E-1 | orange |
| 138 | 2-methylnaphthalene-1,5-disulfonic acid | 6-amino-1-hydroxy-naphthalene-3-sulfonic acid (2-methyl) | Cl | E-2 | orange |
| 139 | 2-methylnaphthalene-1,5-disulfonic acid | 7-amino-1-hydroxy-naphthalene-3-sulfonic acid (2-methyl) | Cl | E-1 | yellowish red |

TABLE 6-continued
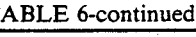
| Ex. No. | D | K | X | E | Hue on cotton |
|---|---|---|---|---|---|
| 140 | | | Cl | E-1 | yellowish red |
| 141 | | | Cl | E-1 | yellowish red |
| 142 | | | Cl | E-1 | red |
| 143 | | | Cl | E-1 | red |
| 144 | | | Cl | E-1 | red |
| 145 | | | Cl | E-1 | red |
| 146 | | | Cl | E-1 | red |

TABLE 6-continued $$D-N=N-K \text{ (triazine with X, NH-E substituents)}$$

| Ex. No. | D | K | X | E | Hue on cotton |
|---|---|---|---|---|---|
| 147 | 6-chloro-triazine with 4-sulfophenylamino and 2,5-disulfo-4-methylphenylamino | 1-hydroxy-2-methyl-6-(methylamino)naphthalene-3-sulfonic acid | Cl | E-1 | red |
| 148 | 7-methylnaphthalene-1,3,6-trisulfonic acid | 4-methyl-3-acetamidoaniline | Cl | E-1 | reddish yellow |
| 149 | 7-methylnaphthalene-1,3,6-trisulfonic acid | 4-methyl-3-acetamidoaniline | F | E-1 | reddish yellow |
| 150 | 7-methylnaphthalene-1,3,6-trisulfonic acid | 4-methyl-3-ureidoaniline | F | E-1 | reddish yellow |
| 151 | 7-methylnaphthalene-1,3,6-trisulfonic acid | 4-methyl-3-ureidoaniline | Cl | E-6 | reddish yellow |
| 152 | 7-methylnaphthalene-1,3,6-trisulfonic acid | 4-methyl-3-ureidoaniline | Cl | E-2 | reddish yellow |
| 153 | 7-methylnaphthalene-1,3,5-trisulfonic acid | 4-methyl-3-ureidoaniline | F | E-3 | reddish yellow |
| 154 | 7-methylnaphthalene-1,3,6-trisulfonic acid | 4-methyl-3-ureidoaniline | Cl | E-5 | reddish yellow |

TABLE 6-continued

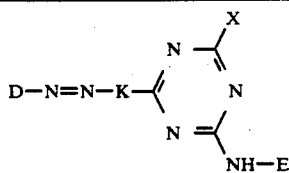

| Ex. No. | D | K | X | E | Hue on cotton |
|---|---|---|---|---|---|
| 155 | 3-methyl-naphthalene-1,6,7-trisulfonic acid (SO₃H positions 1,6; CH₃ at 3; SO₃H at 7) | phenyl with NH— and NH—CONH₂ | Cl | E-7 | reddish yellow |
| 156 | 3-methyl-naphthalene-1,6,7-trisulfonic acid | phenyl with NH— and NH—CO—NH—C₆H₅ | Cl | E-1 | reddish yellow |
| 157 | benzene-2,4-disulfonic acid, methyl | phenyl with NH— and NH—CO—NH—C₆H₅ | Cl | E-1 | yellow |
| 158 | benzene-2,4-disulfonic acid, methyl | phenyl with NH— and NH—CO—NH—C₆H₅ | Cl | E-1 | yellow |
| 159 | benzene-2,4-disulfonic acid, methyl | phenyl with OCH₃, NH—, NH—CO—CH₃ | Cl | E-1 | reddish yellow |
| 160 | benzene-2,4-disulfonic acid, methyl | phenyl with OCH₃, NH—, H₃C | Cl | E-1 | reddish yellow |
| 161 | benzene-2,4-disulfonic acid, methyl | phenyl with OCH₃, NH—, NH—COCH₃ | Cl | E-1 | reddish yellow |
| 162 | 7-methylnaphthalene-1,5-disulfonic acid | phenyl with NH—, NH—COCH₃ | Cl | E-1 | reddish yellow |

TABLE 6-continued $$D-N=N-K\underset{N}{\overset{N}{\diagdown}}\underset{NH-E}{\overset{X}{\diagup}}$$

| Ex. No. | D | K | X | E | Hue on cotton |
|---|---|---|---|---|---|
| 163 | SO₃H-naphthalene-SO₃H (with methyl) | phenyl with NH— and NH—COCH₃ | F | E-1 | reddish yellow |
| 164 | SO₃H-naphthalene-SO₃H (with methyl) | phenyl with OCH₃, NH—, H₃N | Cl | E-1 | reddish yellow |

EXAMPLE 165

7 g of sulfanilamide were dissolved in 200 ml of water and admixed with a mixture of 8 ml of 5N NaNO₂ solution and 10 ml of 10N HCl at 0° C. A suspension of 13.7 g of 1-amino-8-hydroxynaphthalene-3,6-disulfonic acid in 100 ml of water was added dropwise at 0°–5° C. after 1 hour and stirred in at room temperature for 12 hours.

After cooling down to 10° C., the following diazo component was added: 500 ml of aqueous solution of 23.6 g of 4-(2′-sulfatoethylsulfonyl)-3-(2′-sulfatoethylsulfonylmethyl)aniline were admixed at 0° C. with a suspension of 8.5 of cyanuric chloride in 200 ml of ice water by stirring at about 0°–5° C. for 5 hours. This reaction mixture was slowly added to 8.2 g of 1,3-phenylenediamine-4-sulfonic acid, dissolved in 150 ml of H₂O under neutral conditions, at 40° C. The reaction solution was maintained at 40° C. and pH 5–5.5 for 1 hour and then diazotized at 0° C. for 3 hours with 8 ml of 5N NaNO₂ solution, 5 ml of formic acid and 7 ml of 10N HCl. The coupling was carried out at pH 6–7 (maintained with sodium bicarbonate) for 3 hours and was followed by stirring overnight at pH 6.5. The dye was salted out with 200 g of sodium chloride and dried. It has the formula

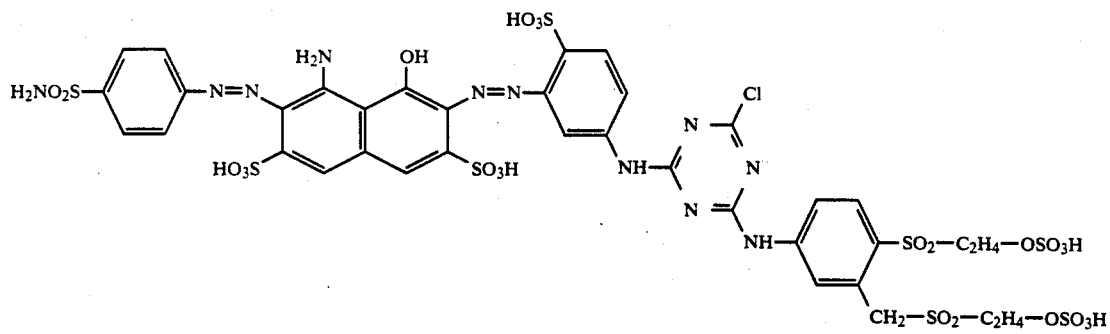

and dyes cotton in fast navy shades.

EXAMPLE 166

Example 165 was repeated, except that the 1-amino-8-hydroxynaphthalene-3,6-disulfonic acid was replaced by 1-amino-8-hydroxynaphthalene-4,6-disulfonic acid, affording a dye having similar properties.

Table 7 contains further dye examples prepared in a similar manner to Example 165.

TABLE 7

Structure:
$D^1-N=N-$ [naphthalene with $H_2N$, $OH$, $HO_3S$, $SO_3H$ groups, positions 3/4] $-N=N-D^2-$ [triazine ring with $X$ and $NH-E$]

| Ex. No. | $D^1$ | Position 3/4 | $D^2$ | X | E | Hue on cotton |
|---|---|---|---|---|---|---|
| 167 | 4-($HO_3S$)-phenyl | 3 | 2-($HO_3S$)-5-(NH—)-phenyl | Cl | E-1 | navy |
| 168 | 4-($HO_3S$)-phenyl | 3 | 2-($HO_3S$)-5-(NH—)-phenyl | F | E-2 | navy |
| 169 | 2-methyl-1,5-disulfonaphthyl | 3 | 2-($HO_3S$)-5-(NH—)-phenyl | Cl | E-1 | navy |
| 170 | 4-($CH_2$=CH—$CH_2$—$SO_2$—)-phenyl | 4 | 2-($HO_3S$)-5-(NH—)-phenyl | Cl | E-1 | navy |
| 171 | 4-($HO_3SO$—$CH_2$—$CH_2$—$SO_2$—)-phenyl | 3 | 2-($HO_3S$)-5-(NH—)-phenyl | Cl | E-1 | navy |
| 172 | 4-($SO_3H$)-3-methyl-phenyl linked via NH—CO-phenyl-N(3,4-dichloro-pyridazinone) | 3 | 2-($HO_3S$)-5-(NH—)-phenyl | Cl | E-1 | navy |
| 173 | 2-($SO_3H$)-5-($CH_3$—$O_2S$—NH)-phenyl | 3 | 2-($HO_3S$)-5-(NH—)-phenyl | Cl | E-1 | navy |

TABLE 7-continued

[Structure: D¹—N=N— attached to naphthalene with H₂N, OH, HO₃S, SO₃H (positions 3/4), —N=N—D²—with triazine bearing NH—E and X]

| Ex. No. | D¹ | Position 3/4 | D² | X | E | Hue on cotton |
|---|---|---|---|---|---|---|
| 174 | HO₂C—C₆H₄— (para) | 3 | HO₃S—C₆H₃(NH—)— | Cl | E-1 | navy |
| 175 | SO₃H—C₆H₄— (ortho) | 3 | HO₃S—C₆H₃(NH—)— | Cl | E-1 | navy |
| 176 | HO₃S—C₆H₄— (meta) | 3 | HO₃S—C₆H₃(NH—)— | Cl | E-1 | navy |

EXAMPLE 177

13.7 g of the sodium salt of 1-amino-8-hydroxynaphthalene-3,6-disulfonic acid, suspended in 100 ml of water, were added at 0°–5° C. to the solution of 0.04 mol of the secondary condensation product of 1,3-phenylenediamine-4-sulfonic acid, cyanuric chloride and 4-(2'-sulfatoethylsulfonyl)-3-(2''-sulfatoethylsulfonylmethyl)-aniline prepared and diazotized as described in Example 165. A pH of from 2.5 to 3 was maintained with sodium formate. The mixture was stirred at room temperature for 12 hours, 7.8 g of aniline-4-sulfonic acid which had been diazotized in the presence of hydrochloric acid was then added at 10° C., dissolved in 200 ml of H₂O, and the pH was maintained with sodium bicarbonate at 6–6.5. Sodium chloride was added to salt out a dye of the formula

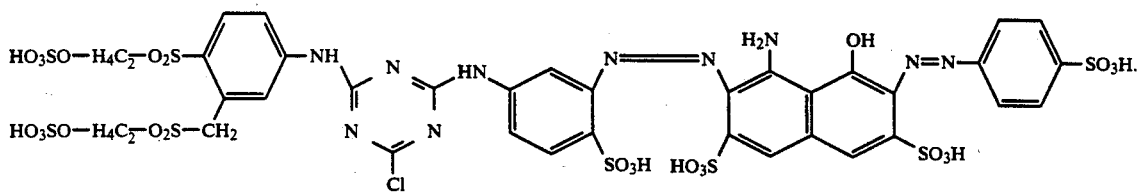

The dyes listed in Table 8 are obtained in a similar manner.

TABLE 8

![Structure: E—NH—[triazine with X]—D¹—N=N—[naphthalene with H₂N, OH, HO₃S, SO₃H at positions 3/4]—N=N—D²]

| Ex. No. | E | X | D¹ | Position 3/4 | D² | Hue on cotton |
|---|---|---|---|---|---|---|
| 178 | E-1 | F | 2-SO₃H-5-(—NH—)phenyl | 3 | 4-(SO₂NH₂)phenyl | navy |
| 179 | E-1 | Cl | 2-SO₃H-5-(—NH—)phenyl | 3 | 4-SO₃H-3-methyl-phenyl—NH—[triazine: Cl, NH—E¹] | navy |
| 180 | E-1 | Cl | 2-SO₃H-5-(—NH—)phenyl | 3 | 2-SO₃H-phenyl | navy |
| 181 | E-1 | Cl | 2-SO₃H-5-(—NH—)phenyl | 3 | 3-SO₃H-phenyl | navy |
| 182 | E-2 | Cl | 2-SO₃H-5-(—NH—)phenyl | 3 | 4-SO₃H-3-methyl-phenyl—NH—[triazine: Cl, NH—E²] | navy |
| 183 | E-3 | Cl | 2-SO₃H-5-(—NH—)phenyl | 3 | 4-SO₃H-3-methyl-phenyl—NH—[triazine: Cl, NH—E³] | navy |

TABLE 8-continued

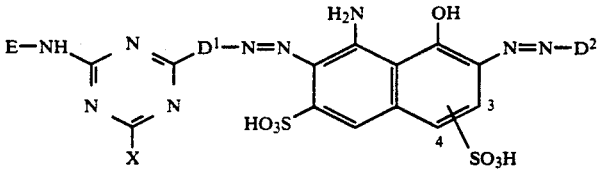

| Ex. No. | E | X | D¹ | Position 3/4 | D² | Hue on cotton |
|---|---|---|---|---|---|---|
| 184 | E-5 | Cl | 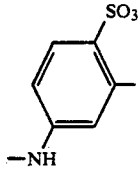 | 3 | 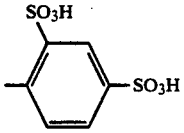 | navy |
| 185 | E-1 | Cl | 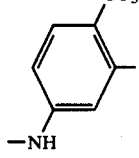 | 4 | 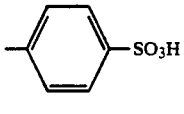 | navy |
| 186 | E-1 | Cl | 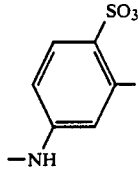 | 3 | —$SO_2$—$CH_2$—CH=$CH_2$ | navy |
| 187 | E-1 | Cl | 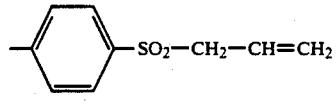 | 4 | —$SO_2$—$C_2H_4$—$OSO_3H$ | navy |

EXAMPLE 188

38.6 g of the known dye of the formula

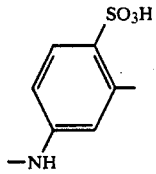

were introduced first in 400 ml of water at neutral pH and 40° C. and admixed with 31.6 g of the primary condensation product of cyanuric chloride and 4-(2'-sulfatoethylsulfonyl)-3-(2''-sulfatoethylsulfonylmethyl-)aniline prepared in Example 81, in 500 ml of water. Stirring was continued at 40° C. and pH 5–6 until there were no longer any free amino groups detectable by thin layer chromatography. The dye obtained on salting out with potassium chloride conforms to the formula

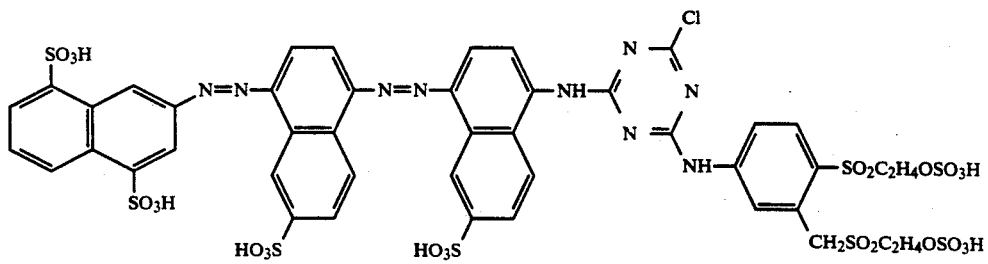

and dyes cotton in reddish brown shades.

Table 9 contains dyes prepared in a similar manner.

TABLE 9

D—N=N—K¹—N=N—K²—NH—(triazine with X, NH—E)

| Ex. No. | D | K¹ | K² | X | E | Hue on cotton |
|---|---|---|---|---|---|---|
| 189 | 2,4-disulfophenyl (SO₃H, HO₃S) | naphthyl-SO₃H | naphthyl-SO₃H | Cl | E-1 | reddish brown |
| 190 | 2,4-disulfophenyl | naphthyl-SO₃H | naphthyl-SO₃H | Cl | E-1 | reddish brown |
| 191 | naphthyl-(SO₃H)₂ | naphthyl | naphthyl-SO₃H | Cl | E-1 | reddish brown |
| 192 | naphthyl-(SO₃H)₂ | 2,5-dimethylphenyl | naphthyl-SO₃H | Cl | E-1 | yellowish brown |
| 193 | naphthyl-(SO₃H)₂ | 2,5-dimethylphenyl | naphthyl-SO₃H | Cl | E-2 | yellowish brown |
| 194 | naphthyl-(SO₃H)₂ | naphthyl-SO₃H | 2,5-dimethylphenyl | F | E-1 | yellowish brown |

TABLE 9-continued $$D-N=N-K^1-N=N-K^2-NH-\underset{\underset{X}{\overset{N}{\nwarrow}}\overset{}{\underset{N}{\searrow}}}{\overset{N}{\diagup}}-NH-E$$

| Ex. No. | D | K¹ | K² | X | E | Hue on cotton |
|---|---|---|---|---|---|---|
| 195 | naphthalene with SO₃H, HO₃S, SO₃H substituents | naphthalene | naphthalene with HO₃S | Cl | E-1 | reddish brown |
| 196 | E¹ | naphthalene with HO₃S | naphthalene with HO₃S | Cl | benzene with SO₃H, HO₃S | reddish brown |
| 197 | benzene with SO₃H, HO₃S | naphthalene with HO₃S | naphthalene with SO₃H | Cl | E-1 | reddish brown |
| 198 | naphthalene with SO₃H, HO₃S | naphthalene with HO₃S | naphthalene with HO₃S | Cl | E-1 | reddish brown |
| 199 | benzene with SO₃H, CH₃SO₂NH | naphthalene with HO₃S | naphthalene with HO₃S | Cl | E-1 | reddish brown |

EXAMPLE 200

64.8 g of the known dye of the formula

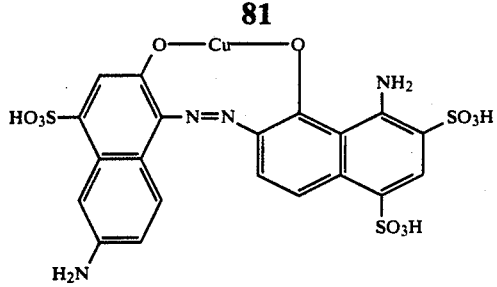

were suspended in 700 ml of water. 31.6 g of the primary condensation product of cyanuric chloride and 4-(2'-sulfatoethylsulfonyl)-3-(2''-sulfatoethylsulfonylmethyl)-aniline described in Example 81 were added dissolved in 800 ml of water at pH 5.5–6 and 40° C. over 2 hours, and the resulting mixture was maintained at pH 5.5–6 and 40°–45° C. for a further 30 minutes. After the reaction had ended, the dye was salted out with sodium chloride, filtered off and dried under reduced pressure. It conforms to the formula

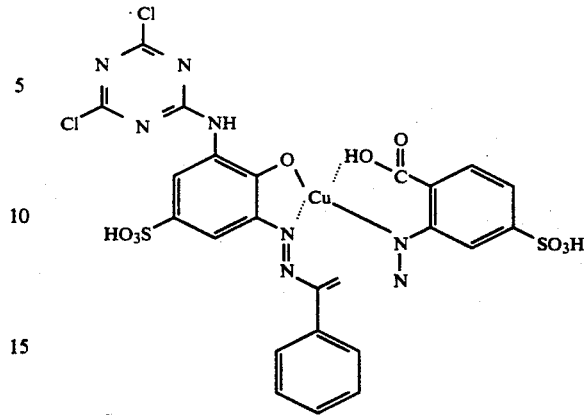

in 600 ml of water was added at pH 7 a solution of 49 g of 4-(2'-sulfatoethylsulfonyl)-3-(2''-sulfatoethylsulfonylmethyl)aniline in 600 ml of water. The suspension as heated at 40°–45° C., and the pH was kept neutral by the addition of NaHCO₃. After 2.5 hours the resulting dye which conforms to the formula

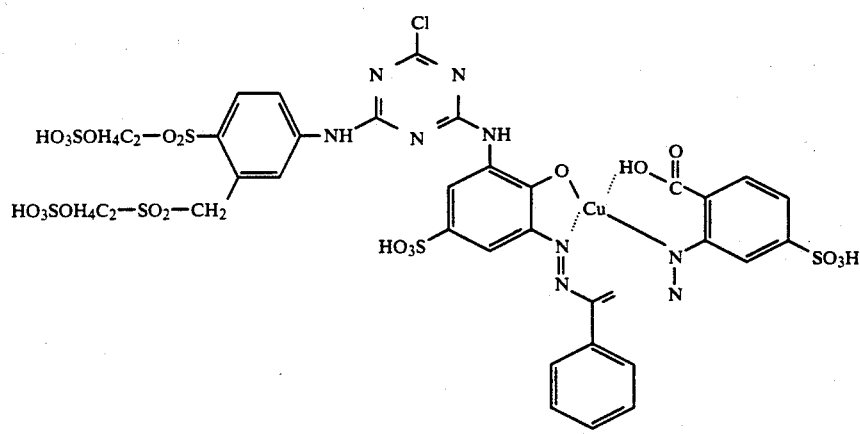

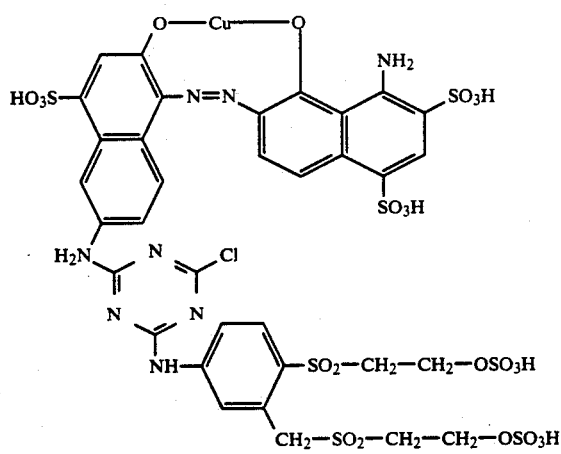

and dye cotton in fast blue shades.

EXAMPLE 201

To a suspension of 75 g of the known dichlorotriazine dye of the formula was salted out with 250 g of sodium chloride, filtered off and dried. The dark blue dye powder obtained dyes cotton in bright blue shades. The dyeings are light- and wet-fast, and they show remarkable stability to oxidative influences.

The method described in Example 201 can also be used to prepare the dyes of the formula

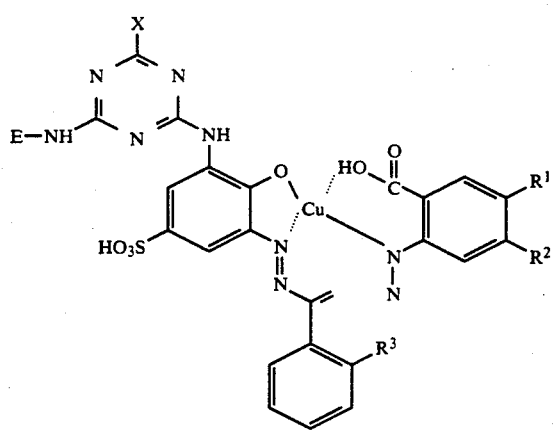

listed in Table 10.

TABLE 10

| Example | E | X | R¹ | R² | R³ |
|---|---|---|---|---|---|
| 202 | E-2 | Cl | H | SO₃H | H |
| 203 | E-3 | Cl | H | SO₃H | H |
| 204 | E-1 | Cl | SO₃H | H | H |
| 205 | E-2 | Cl | SO₃H | H | H |
| 206 | E-3 | Cl | SO₃H | H | H |
| 207 | E-1 | Cl | SO₃H | H | SO₃H |
| 208 | E-1 | Cl | H | SO₃H | SO₃H |

EXAMPLE 209

43.4 g of 88% strength 1-amino-4-bromoanthraquinone-2-sulfonic acid, 39 g of the amine of the formula

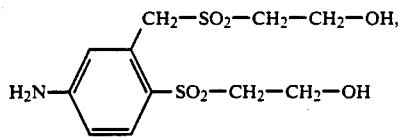

1.5 g of Cu powder, 0.75 g of Cu(II) sulfate and 50.4 g of sodium bicarbonate were heated at 65°–70° C. for 120 hours. After complete conversion (thin layer chromatography), the mixture was filtered hot, and the filtrate was brought to pH 1 with concentrated hydrochloric acid. The oily residue was crystallized at 0°–5° C. by stirring out with 100 ml of ethanol, and the crystalline product was isolated, washed with ethanol and dried. This gave 45 g of a compound of the formula

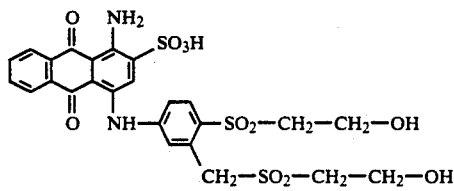

The same method can be used to obtain the compounds of the formula

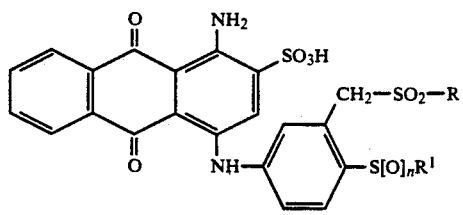

TABLE 11

| Example No. | R | R¹ | n |
|---|---|---|---|
| 210 | CH₂CH₂OH | CH₂CH₂OH | 0 |
| 211 | CH₂CH₂OH | CH₂CH₂OH | 1 |
| 212 | CH₂CH₂OH | CH₂CH(CH₃)OH | 0 |
| 213 | CH₂CH₂OH | CH₂CH(CH₃)OH | 1 |
| 214 | CH₂CH₂OH | CH₂CH(CH₃)OH | 2 |
| 215 | CH₂CH(CH₃)OH | CH₂CH₂OH | 0 |
| 216 | CH₂CH(CH₃)OH | CH₂CH₂OH | 1 |
| 217 | CH₂CH(CH₃)OH | CH₂CH₂OH | 2 |
| 218 | CH₂CH(CH₃)OH | CH₂CH(CH₃)OH | 0 |
| 219 | CH₂CH(CH₃)OH | CH₂CH(CH₃)OH | 1 |
| 220 | CH₂CH(CH₃)OH | CH₂CH(CH₃)OH | 2 |

EXAMPLE 221

10 g of the compound of the formula

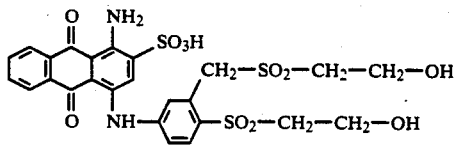

obtained in Example 209 were stirred in 40 g of chlorosulfonic acid at 20°–25° C. for 3 hours. The melt was precipitated onto 400 g of ice/water, and the mixture was brought to pH 5 with sodium bicarbonate. The solution was spray-dried to leave a product which, besides salt, contained the dye of the formula

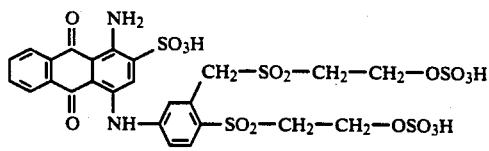

Brilliant blue dyeings having good fastness properties were obtained on cotton.

The same method can be used to obtain the dyes of the formula

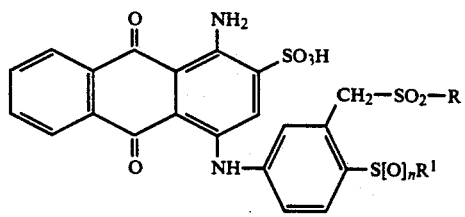

listed in Table 12.

TABLE 12

| Example No. | R | R¹ | n |
|---|---|---|---|
| 222 | CH₂CH₂OSO₃H | CH₂CH₂OSO₃H | 0 |
| 223 | CH₂CH₂OSO₃H | CH₂CH₂OSO₃H | 1 |
| 224 | CH₂CH₂OSO₃H | CH₂CH(CH₃)OSO₃H | 0 |

TABLE 12-continued

| Example No. | R | R¹ | n |
|---|---|---|---|
| 225 | $CH_2CH_2OSO_3H$ | $CH_2CH(CH_3)OSO_3H$ | 1 |
| 226 | $CH_2CH_2OSO_3H$ | $CH_2CH(CH_3)OSO_3H$ | 2 |
| 227 | $CH_2CH_3OSO_3H$ | $CH_2CH(CH_3)OSO_3H$ | 0 |
| 228 | $CH_2CH_3OSO_3H$ | $CH_2CH(CH_3)OSO_3H$ | 1 |
| 229 | $CH_2CH_3OSO_3H$ | $CH_2CH(CH_3)OSO_3H$ | 2 |
| 230 | $CH_2CH_3OSO_3H$ | $CH_2CH_2OSO_3H$ | 0 |
| 231 | $CH_2CH_3OSO_3H$ | $CH_2CH_2OSO_3H$ | 1 |
| 232 | $CH_2CH_3OSO_3H$ | $CH_2CH_2OSO_3H$ | 2 |

EXAMPLE 233

19.1 g of the compound of the formula

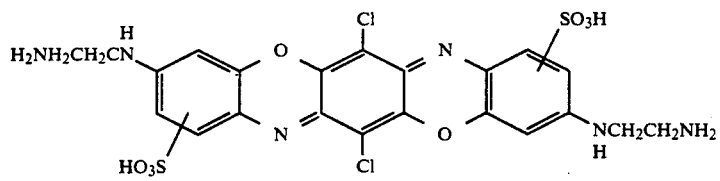

were stirred into 1000 g of water set to pH 10 with sodium hydroxide solution. This solution was added dropwise to a hot solution at 60° C. and pH 6–8 of the condensation product of 13.5 g of cynauric chloride and 31.9 g of 4-(2'-sulfatoethylsulfonyl)-5-(2''-sulfatoethyl-sulfonylmethyl)aniline. While a pH of 6.5–7 was maintained, stirring ws continued at 60° C. until the reaction had ended, which took about 1 hour (thin layer chromatography). After cooling down to room temperature, the dye was salted out with 500 g of NaCl, filtered off with suction and dried. It dyes cotton in brilliant blue shades having good fastness properties and conforms to the formula

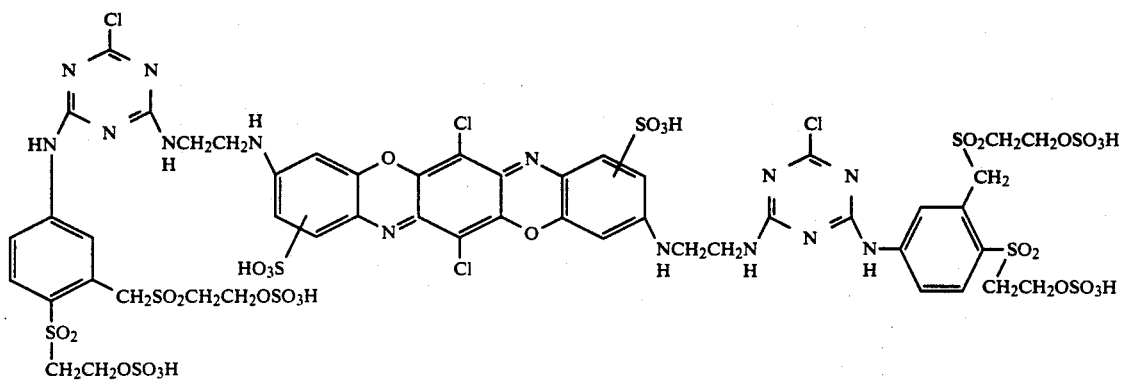

Further dyes obtained in a similar manner are given in Table 13.

TABLE 13

| Example No. | Y | X | R | E | Hue on cotton |
|---|---|---|---|---|---|
| 234 | HN–CH(CH₃)–NH | $SO_3H$ | Cl | E-1 | blue |
| 235 | HN–CH₂CH₂–NH | $SO_3H$ | F | E-1 | blue |
| 236 | HN–(CH₂)₃–NH | $SO_3H$ | Cl | E-1 | blue |
| 237 | HN–C₆H₄–NH (para) | $SO_3H$ | Cl | E-1 | blue |
| 238 | HN–CH₂CH₂–NH | $SO_2C_2H_4OSO_3H$ | Cl | E-1 | blue |

TABLE 13-continued

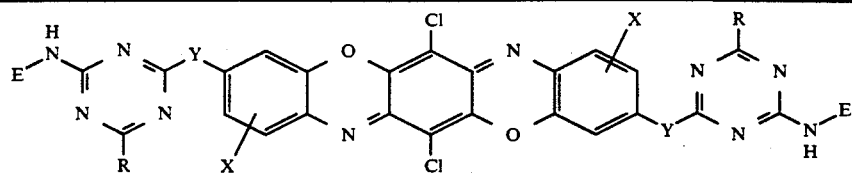

| Example No. | Y | X | R | E | Hue on cotton |
|---|---|---|---|---|---|
| 239 | O-CH2CH2-NH | SO3H | Cl | E-1 | red |
| 240 | O-C6H4-NH (para) | SO3H | Cl | E-1 | red |
| 241 | HN-CH2CH2-NH | SO3H | Cl | E-2 | blue |
| 242 | HN-CH2CH2-NH | SO3H | F | E-2 | blue |
| 243 | HN-CH2-CH(CH3)-NH | SO3H | Cl | E-2 | blue |
| 244 | HN-CH2CH2CH2-NH | SO3H | Cl | E-2 | blue |
| 245 | HN-C6H4-NH (para) | SO3H | Cl | E-2 | blue |
| 246 | HN-CH2CH2-NH | SO2C2H4OSO3H | Cl | E-2 | blue |
| 247 | O-CH2CH2-NH | SO3H | Cl | E-2 | red |
| 248 | O-C6H4-NH (para) | SO3H | Cl | E-2 | red |
| 249 | HN-CH2CH2-NH | SO3H | Cl | E-3 | blue |
| 250 | HN-CH2CH2-NH | SO3H | F | E-3 | blue |
| 251 | HN-CH2-CH(CH3)-NH | SO3H | Cl | E-3 | blue |
| 252 | HN-CH2CH2CH2-NH | SO3H | Cl | E-3 | blue |
| 253 | HN-C6H4-NH (para) | SO3H | Cl | E-3 | blue |
| 254 | HN-CH2CH2-NH | SO2C2H4OSO3H | Cl | E-3 | blue |
| 255 | O-CH2CH2-NH | SO3H | Cl | E-3 | red |

TABLE 13-continued

[Structure with Y, X, R, E substituents on bridged bis-triazinyl compound]

| Example No. | Y | X | R | E | Hue on cotton |
|---|---|---|---|---|---|
| 256 | O-C6H4-NH | SO3H | Cl | E-3 | red |

EXAMPLE 257

To a neutral solution of 48 g of 4-(2'-sulfatoethylsulfonyl)-5-(2"-sulfatoethylsulfonylmethyl)aniline in 200 ml of water were added at from 5°–10° C. 97 g of copper phthalocyaninetetrasulfonyl chloride as a moist presscake. The mixture was stirred at 20°–25° C. for 12 hours while the pH was maintained at 6.5–7.3 by addition of 10% strength sodium carbonate solution. The mixture was then filtered off with suction, the filter residue was dried, leaving 47 g of the dye of the formula

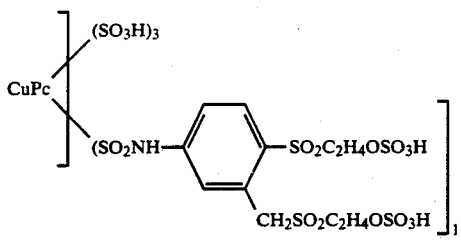

which contained 2.7% of NaCl. The dye dyes cotton in greenish blue shades.

EXAMPLE 258

97 g of copper phthalocyaninetetrasulfonyl chloride were suspended in 750 ml of water at 0°–5° C. 20.5 g of monoacetylethylenediamine were added, and the pH was maintained at 7.3–7.5 with 10% strength sodium carbonate solution. After 12 hours at 20°–25° C., the pH was raised to 10 by addition of sodium hydroxide solution, and the mixture was stirred at 95° C. for one hour. Concentrated hydrochloric acid was added to bring down a precipitate. The precipitate was filtered off with suction, washed with about 2% strength hydrochloric acid and stirred up in 500 ml of water. The pH of the solution was brought to 7.0–7.2 with sodium hydroxide solution, and 21.2 g of cyanuric chloride were added at 0°–5° C. The pH was maintained at 6.5–7.0 by the dropwise addition of sodium carbonate solution. After 3 hours 49 g of 4-(2'-sulfatoethylsulfonyl)-5-(2"-sulfatoethylsulfonylmethyl)-aniline were added, and the temperature was raised to 35°–40° C. The dye solution was spray-dried, giving 185 g of the dye of the formula

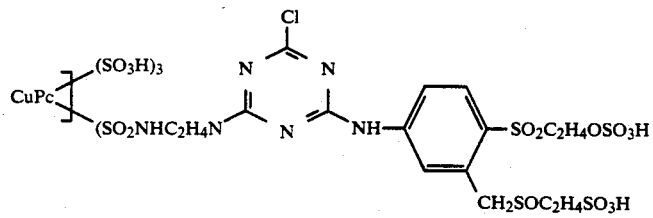

The dye dyes cotton in greenish blue shades.

EXAMPLE 259

97 g of copper phthalocyaninetetrasulfonyl chloride were suspended in 600 ml of water at 0°–5° C. 41 g of N-monoacetyl-m-phenylenediamine were added, and the pH was maintained at 6.8–7.0 by addition of 10% strength sodium carbonate solution. 12 g of 25% strength ammonia solution and 16 g of sodium acetate were then added, and the temperature was raised to 50° C. in the course of 3 hours and the pH was maintained at 7.0. 250 g of concentrated HCl were added, and the temperature was raised to 90°–95° C. After 4 hours, the mixture was cooled down, and the resulting precipitate was filtered off with suction and washed neutral. Without drying, the precipitate was suspended in 750 ml of water, and 19.4 g of cyanuric chloride were added at pH 7.0 and 0–°5° C. The pH was maintained at 6.5–7.0 by the addition of sodium carbonate solution. After 3 hours 49 g of 4-(2'-sulfatoethylsulfonyl)-5-(2"-sulfatoethylsulfonylmethyl)-aniline were added, and the temperature was raised to 35°–40° C. The dye solution was spray-dried, giving 260 g of the dye of the formula

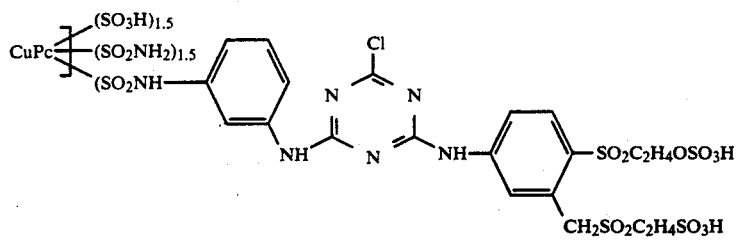

which dyes cotton in greenish blue shades.

EXAMPLE 260

350 g of 5-nitro-2-chlorobenzyl chloride, 136 g of 2-mercaptoethanol and 234.5 g of potassium carbonate were stirred in 1700 ml of water at 40° C. for 4 hours and at 60° C. for 1 hour. The reaction solution was brought to pH 6 with acetic acid and, after the addition of 10 g of tungstic acid, admixed with 2060 g of 15% strength hydrogen peroxide solution at 55° C. After the exothermic reaction had ended, the mixture was stirred at 85° C. for 3 hours and at 20° C. for 12 hours. The precipitated product was isolated, washed with water and dried under reduced pressure at 50° C., leaving 395 g of an analytically pure product of the following constitution:

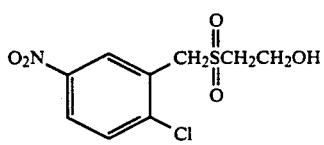

Analysis Calc.: chlorine covalent 12.7% found: 12.4% melting point: 127°–128° C.

If instead of 2-mercaptoethanol the same molar amount of 1-mercaptopropan-2-ol was used, then an analytically pure product of the formula (260a)

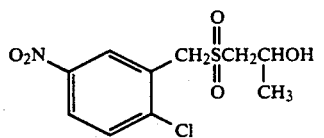

melting point: 121°–122° C. was obtained.

The same method was used to prepare the following intermediates:

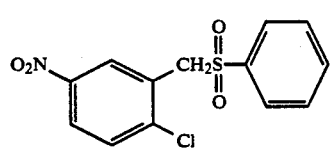 (260b)

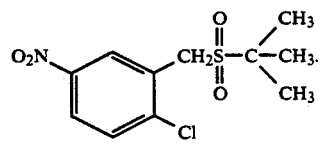 (260c)

29.8 g of 4-nitro-1-chloro-2-benzyl β-hydroxyethyl sulfone obtained in Example 260 and 3.3 g of paraformaldehyde were heated to 60° C. in 100 ml of methanol. 19.8 g of 30% strength sodium methoxide solution were added dropwise at that temperature in the course of 0.5 hours. After 3 hours' stirring at 60°–65° C. the mixture was cooled down to 20°–25° C., and the precipitated product was isolated, washed with water and dried, leaving 20 g of an analytically pure product of the formula

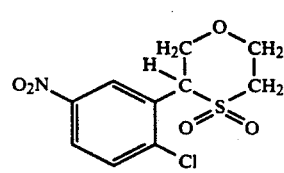

Analysis calc.: chlorine covalent 12.2% found: 12.1%
melting point: 224° C.

EXAMPLE 262

59.5 g of 4-nitro-1-chloro-2-benzyl β-hydroxyethyl sulfone obtained in Example 260 were dissolved in 100 ml of N-methylpyrrolidinone. To the cold solution at 0° C. was added dropwise a freshly prepared solution of 17.2 g of thioethanol, 12.3 g of potassium hydroxide and 100 ml of N-methylpyrrolidinone. After 12 hours' stirring at 20°–25° C. the solvent was distilled off under reduced pressure, 200 ml of water were added to the residue, and the mixture was brought to pH 6 with acetic acid. After 2 hours' stirring at 0°–5° C. the precipitated product was isolated, washed with water ad dried, leaving 60 g of a product which predominantly conformed to the formula

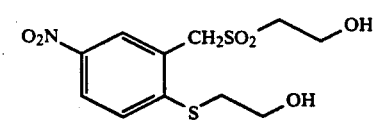

melting point: 126°–128° C.

The following compounds are obtained by the method of Example 262 from the intermediates described in Examples 260 and 261:

TABLE 14

$$O_2N-\text{C}_6H_3(SR^2)-CHR-SO_2R^1$$

| Example No. | R | $R^1$ | $R^2$ |
|---|---|---|---|
| 263 | H | —CH₂CH₂OH | —CH₂CH₂OH |
| 264 | H | —CH₂CH₂OH | —CH₂CH(CH₃)OH |
| 265 | H | —CH₂CH₂OH | —C(CH₃)₃ |
| 266 | H | —CH₂CH₂OH | —Ph |

TABLE 14-continued

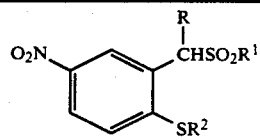

| Example No. | R | R¹ | R² |
|---|---|---|---|
| 267 | H | —CH₂CH(CH₃)OH | —CH₂CH₂OH |
| 268 | H | —CH₂CH(CH₃)OH | —CH₂CH(CH₃)OH |
| 269 | H | —CH₂CH(CH₃)OH | —C(CH₃)₃ |
| 270 | H | —CH₂CH(CH₃)OH | —Ph |
| 271 | H | —C(CH₃)₃ | —CH₂CH₂OH |
| 272 | H | —C(CH₃)₃ | —CH₂CH(CH₃)OH |
| 273 | H | —Ph | —CH₂CH₂OH |
| 274 | H | —Ph | —CH₂CH(CH₃)OH |
| 275 | —CH₂—O—CH₂—CH₂— | | —CH₂CH₂OH |
| 276 | —CH₂—O—CH₂—CH₂— | | —CH₂CH(CH₃)OH |

EXAMPLE 277

32.1 g of the compound of the formula

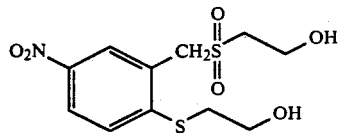

described in Example 262 were dissolved in 200 ml of water at 40° C. and oxidized by addition of 0.5 g of tungstic acid and molar amounts of hydrogen peroxide. After 2 hours' stirring at 40° C., the mixture was cooled down to 0°–5° C., and the precipitated product was isolated, washed with water and dried at 40° C. under reduced pressure, leaving 30.2 g of a product which predominantly conformed to the formula

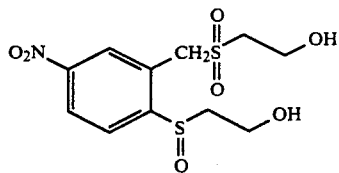

melting point: 58°–61° c.

The same method can be used to give the compounds described in Table 15.

TABLE 15

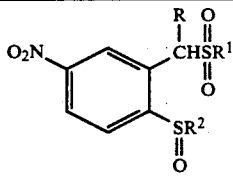

| Example No. | R | R¹ | R² |
|---|---|---|---|
| 278 | H | —CH₂CH₂OH | —CH₂CH₂OH |
| 279 | H | —CH₂CH₂OH | —CH₂CH(CH₃)OH |
| 280 | H | —CH₂CH₂OH | —C(CH₃)₃ |
| 281 | H | —CH₂CH₂OH | —Ph |
| 282 | H | —CH₂CH(CH₃)OH | —CH₂CH₂OH |
| 283 | H | —CH₂CH(CH₃)OH | —CH₂CH(CH₃)OH |
| 284 | H | —CH₂CH(CH₃)OH | —C(CH₃)₃ |
| 285 | H | —CH₂CH(CH₃)OH | —Ph |
| 286 | H | —C(CH₃)₃ | —CH₂CH₂OH |

TABLE 15-continued

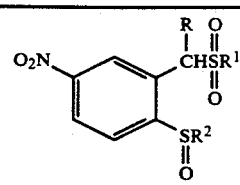

| Example No. | R | R¹ | R² |
|---|---|---|---|
| 287 | H | —C(CH₃)₃ | —CH₂CH(CH₃)OH |
| 288 | H | —Ph | —CH₂CH₂OH |
| 289 | H | —Ph | —CH₂CH(CH₃)OH |
| 290 | —CH₂—O—CH₂—CH₂— | | —CH₂CH₂OH |
| 291 | —CH₂—O—CH₂—CH₂— | | —CH₂CH(CH₃)OH |

EXAMPLE 292

59.5 g of 4-nitro-1-chloro-2-benzyl β-hydroxyethyl sulfone obtaine din Example 260 were dissolved in 100 ml of N-methylpyrrolidinone. To the cold solution at 0° C. was added dropwise a freshly prepared solution of 17.2 g of thioethanol, 12.3 g of potassium hydroxide and 100 ml of N-methylpyrrolidinone. After 12 hours' stirring at 20°–25° C. the solvent was distilled off under reduced pressure, and the residue was admixed with 200 ml of water and heated to 40° C. The solution was brought to pH 6 with acetic acid and, after addition of 0.8 g of tungstic acid, oxidized with the molar amount of hydrogen peroxide. After 2 hours' stirring at 40° C., the mixture was cooled down to 0°–5° C., and the precipitated product was isolated, washed with water and dried at 40° C. under reduced pressure. This left 60.9 g of a product which conformed to the compound of the formula

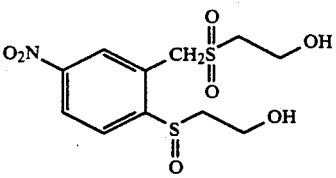

melting point: 58°–61° C.
described in Example 277.

The compounds described in Table 15 may also be obtained by the method described above.

EXAMPLE 293

963 g of 4-nitro-1-chloro-2-benzyl β-hydroxyethyl sulfone obtained in Example 260 were dissolved in 1500 ml of N-methylpyrrolidinone. To the cold solution at 0° C. was added dropwise a freshly prepared solution of 297 g of thioethanol, 212 g of potassium hydroxide and 1500 ml of N-methylpyrrolidinone in the course of 3 hours. After 12 hours' stirring at 20°–25° C. the solvent was distilled off under reduced pressure, and the residue was admixed with 3000 ml of water, heated to 40° C. and, after the addition of 10 g of tungstic acid, oxidized with 2100 g of 30% strength hydrogen peroxide solution. After the exothermic reaction had ended, the mixture was stirred at 60° C. for 2 hours, at 80° C. for another 2 hours and at 95° C. for 1 hour, and cooled down to 20°–25° C. The precipitated product was isolated, washed with water and dried at 40° C. under reduced pressure, leaving 1005 g of product conforming to the formula

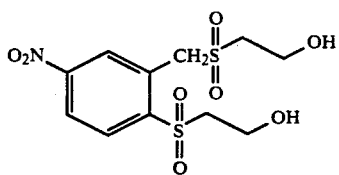

melting point: 139°–142° C.

The intermediates described in Examples 260 and 261 can be converted by the method of Example 293 into the compounds listed in Table 16.

TABLE 16

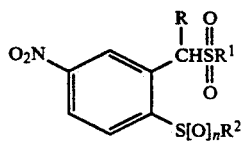

| Ex. No. | R | R¹ | R² |
|---|---|---|---|
| 294 | H | —CH₂CH₂OH | —CH₂CH(CH₃)OH |
| 295 | H | —CH₂CH₂OH | —C(CH₃)₃ |
| 296 | H | —CH₂CH₂OH | —Ph |
| 297 | H | —CH₂CH(CH₃)OH | —CH₂CH₂OH |
| 298 | H | —CH₂CH(CH₃)OH | —CH₂CH(CH₃)OH |
| 299 | H | —CH₂CH(CH₃)OH | —C(CH₃)₃ |
| 300 | H | —CH₂CH(CH₃)OH | —Ph |
| 301 | H | —C(CH₃)₃ | —CH₂CH₂OH |
| 302 | H | —C(CH₃)₃ | —CH₂CH(CH₃)OH |
| 303 | H | —Ph | —CH₂CH₂OH |
| 304 | H | —Ph | —CH₂CH(CH₃)₃OH |
| 305 | —CH₂O—CH₂—CH₂— | | —CH₂CH₂OH |
| 306 | —CH₂O—CH₂—CH₂— | | —CH₂CH(CH₃)₃OH |

EXAMPLE 307

32.1 g of the compound described in Example 262 were dissolved in 100 ml of water at 40° C. and, after the addition of 0.5 g of tungstic acid, oxidized with 70 g of 30% strength hydrogen peroxide solution. After the exothermic reaction had ended, the mixture was stirred at 60° C. for 2 hours and then at 80° C. for a further 2 hours. After cooling down to 20°–25° C. the precipitated product was isolated, washed with water and dried at 40° C. under reduced pressure, leaving 34 g of a product which conformed to the compound of the formula

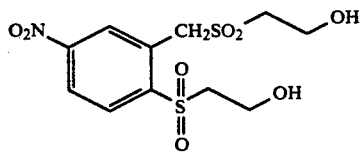

melting point: 139°–142° C.
described in Example 293.

The compounds described in Table 14 can be converted by the method of Example 307 into the compounds listed in Table 15.

EXAMPLE 308

50 g of the compound described in Example 307, 142 ml of thionyl chloride, 500 ml of toluene and 2 ml of dimethylformamide were stirred at 65° C. for 1 hour and at 85° C. for 2 hours. After cooling down to 5°–10° C. the precipitated product was isolated, washed with water and dried at 60° C. under reduced pressure, leaving 54 g of a product conforming to the formula

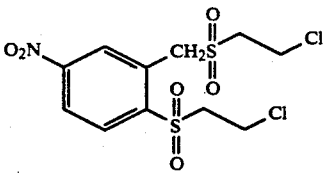

melting point: 158° C.

The products listed in Tables 14, 15 and 16 can be converted by the method of Example 308 into compounds of the formula

TABLE 17

| Ex. No. | R | R¹ | R² | n |
|---|---|---|---|---|
| 309 | H | —CH₂CH₂Cl | —CH₂CH₂Cl | 0 |
| 310 | H | —CH₂CH₂Cl | —CH₂CH₂Cl | 1 |
| 311 | H | —CH₂CH₂Cl | —CH₂CH(CH₃)Cl | 0 |
| 312 | H | —CH₂CH₂Cl | —CH₂CH(CH₃)Cl | 1 |
| 313 | H | —CH₂CH₂Cl | —CH₂CH(CH₃)Cl | 2 |
| 314 | H | —CH₂CH₂Cl | —Ph | 0 |
| 315 | H | —CH₂CH₂Cl | —Ph | 1 |
| 316 | H | —CH₂CH₂Cl | —Ph | 2 |
| 317 | H | —CH₂CH₂Cl | —C(CH₃)₃ | 0 |
| 318 | H | —CH₂CH₂Cl | —C(CH₃)₃ | 1 |
| 319 | H | —CH₂CH₂Cl | —C(CH₃)₃ | 2 |
| 320 | H | —CH₂CH(CH₃)Cl | —CH₂CH₂Cl | 0 |
| 321 | H | —CH₂CH(CH₃)Cl | —CH₂CH₂Cl | 1 |
| 322 | H | —CH₂CH(CH₃)Cl | —CH₂CH₂Cl | 2 |
| 323 | H | —CH₂CH(CH₃)Cl | —CH₂CH(CH₃)Cl | 0 |
| 324 | H | —CH₂CH(CH₃)Cl | —CH₂CH(CH₃)Cl | 1 |
| 325 | H | —CH₂CH(CH₃)Cl | —CH₂CH(CH₃)Cl | 2 |
| 326 | H | —CH₂CH(CH₃)Cl | —Ph | 0 |
| 327 | H | —CH₂CH(CH₃)Cl | —Ph | 1 |
| 328 | H | —CH₂CH(CH₃)Cl | —Ph | 2 |
| 329 | H | —CH₂CH(CH₃)Cl | —C(CH₃)₃ | 0 |
| 330 | H | —CH₂CH(CH₃)Cl | —C(CH₃)₃ | 1 |
| 331 | H | —CH₂CH(CH₃)Cl | —C(CH₃)₃ | 2 |
| 332 | H | —C(CH₃)₃ | —CH₂CH₂Cl | 0 |
| 333 | H | —C(CH₃)₃ | —CH₂CH₂Cl | 1 |
| 334 | H | —C(CH₃)₃ | —CH₂CH₂Cl | 2 |
| 335 | H | —C(CH₃)₃ | —CH₂CH(CH₃)Cl | 0 |
| 336 | H | —C(CH₃)₃ | —CH₂CH(CH₃)Cl | 1 |
| 337 | H | —C(CH₃)₃ | —CH₂CH(CH₃)Cl | 2 |
| 338 | H | —Ph | —CH₂CH₂Cl | 0 |
| 339 | H | —Ph | —CH₂CH₂Cl | 1 |
| 340 | H | —Ph | —CH₂CH₂Cl | 2 |
| 341 | H | —Ph | —CH₂CH(CH₃)Cl | 0 |
| 342 | H | —Ph | —CH₂CH(CH₃)Cl | 1 |
| 343 | H | —Ph | —CH₂CH(CH₃)Cl | 2 |
| 344 | —CH₂O—CH₂CH₂— | | —CH₂CH₂Cl | 0 |
| 345 | —CH₂O—CH₂CH₂— | | —CH₂CH₂Cl | 1 |
| 346 | —CH₂O—CH₂CH₂— | | —CH₂CH₂Cl | 2 |
| 347 | —CH₂O—CH₂CH₂— | | —CH₂CH(CH₃)Cl | 0 |
| 348 | —CH₂O—CH₂CH₂— | | —CH₂CH(CH₃)Cl | 1 |

TABLE 17-continued

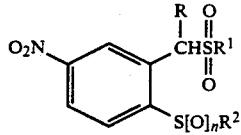

| Ex. No. | R | R¹ | R² | n |
|---|---|---|---|---|
| 349 | —CH₂O—CH₂CH₂— | | —CH₂CH(CH₃)Cl | 2 |

EXAMPLE 350

160 g of the compound described in Example 293 were catalytically reduced with Raney nickel at 25°-30° C. in 1000 ml of methanol. After the reduction had ended, the Raney nickel was separated off and the methanol was distilled off, leaving the amine of the formula

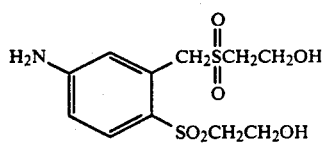

melting point: 112°-113° C.
as an oil which crystallized at 0°-5° C. in the course of one hour.

By the same method it is possible to obtain the following amines of the formula:

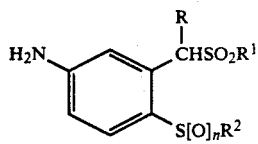

TABLE 18

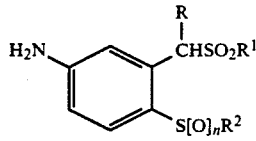

| Ex. No. | R | R¹ | R² | n |
|---|---|---|---|---|
| 351 | H | —CH₂CH₂OH | —CH₂CH₂OH | 0 |
| 352 | H | —CH₂CH₂OH | —CH₂CH₂OH | 1 |
| 353 | H | —CH₂CH₂OH | —CH₂CH(CH₃)OH | 0 |
| 354 | H | —CH₂CH₂OH | —CH₂CH(CH₃)OH | 1 |
| 355 | H | —CH₂CH₂OH | —CH₂CH(CH₃)OH | 2 |
| 356 | H | —CH₂CH₂OH | —Ph | 0 |
| 357 | H | —CH₂CH₂OH | —Ph | 1 |
| 358 | H | —CH₂CH₂OH | —Ph | 2 |
| 359 | H | —CH₂CH₂OH | —C(CH₃)₃ | 0 |
| 360 | H | —CH₂CH₂OH | —C(CH₃)₃ | 1 |
| 361 | H | —CH₂CH₂OH | —C(CH₃)₃ | 2 |
| 362 | H | —CH₂CH(CH₃)OH | —CH₂CH₂OH | 0 |
| 363 | H | —CH₂CH(CH₃)OH | —CH₂CH₂OH | 1 |
| 364 | H | —CH₂CH(CH₃)OH | —CH₂CH₂OH | 2 |
| 365 | H | —CH₂CH(CH₃)OH | —CH₂CH(CH₃)OH | 0 |
| 366 | H | —CH₂CH(CH₃)OH | —CH₂CH(CH₃)OH | 1 |
| 367 | H | —CH₂CH(CH₃)OH | —CH₂CH(CH₃)OH | 2 |
| 368 | H | —CH₂CH(CH₃)OH | —Ph | 0 |
| 369 | H | —CH₂CH(CH₃)OH | —Ph | 1 |
| 370 | H | —CH₂CH(CH₃)OH | —Ph | 2 |
| 371 | H | —CH₂CH(CH₃)OH | —C(CH₃)₃ | 0 |
| 372 | H | —CH₂CH(CH₃)OH | —C(CH₃)₃ | 1 |
| 373 | H | —CH₂CH(CH₃)OH | —C(CH₃)₃ | 2 |
| 374 | H | —C(CH₃)₃ | —CH₂CH₂OH | 0 |

TABLE 18-continued

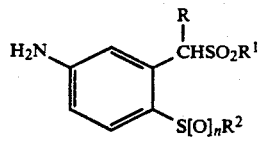

| Ex. No. | R | R¹ | R² | n |
|---|---|---|---|---|
| 375 | H | —C(CH₃)₃ | —CH₂CH₂OH | 1 |
| 376 | H | —C(CH₃)₃ | —CH₂CH₂OH | 2 |
| 377 | H | —C(CH₃)₃ | —CH₂CH(CH₃)OH | 0 |
| 378 | H | —C(CH₃)₃ | —CH₂CH(CH₃)OH | 1 |
| 379 | H | —C(CH₃)₃ | —CH₂CH(CH₃)OH | 2 |
| 380 | H | —Ph | —CH₂CH₂OH | 0 |
| 381 | H | —Ph | —CH₂CH₂OH | 1 |
| 382 | H | —Ph | —CH₂CH₂OH | 2 |
| 383 | H | —Ph | —CHCH(CH₃)OH | 0 |
| 384 | H | —Ph | —CHCH(CH₃)OH | 1 |
| 385 | H | —Ph | —CHCH(CH₃)OH | 2 |
| 386 | H | —CH₂CH₂Cl | —CH₂CH₂Cl | 0 |
| 387 | H | —CH₂CH₂Cl | —CH₂CH₂Cl | 1 |
| 388 | H | —CH₂CH₂Cl | —CH₂CH₂Cl | 2 |
| 389 | H | —CH₂CH₂Cl | —CH₂CH(CH₃)Cl | 0 |
| 390 | H | —CH₂CH₂Cl | —CH₂CH(CH₃)Cl | 1 |
| 391 | H | —CH₂CH₂Cl | —CH₂CH(CH₃)Cl | 2 |
| 392 | H | —CH₂CH₂Cl | —Ph | 0 |
| 393 | H | —CH₂CH₂Cl | —Ph | 1 |
| 394 | H | —CH₂CH₂Cl | —Ph | 2 |
| 395 | H | —CH₂CH₂Cl | —C(CH₃)₃ | 0 |
| 396 | H | —CH₂CH₂Cl | —C(CH₃)₃ | 1 |
| 397 | H | —CH₂CH₂Cl | —C(CH₃)₃ | 2 |
| 398 | H | —CH₂CH(CH₃)Cl | —CH₂CH₂Cl | 0 |
| 399 | H | —CH₂CH(CH₃)Cl | —CH₂CH₂Cl | 1 |
| 400 | H | —CH₂CH(CH₃)Cl | —CH₂CH₂Cl | 2 |
| 401 | H | —CH₂CH(CH₃)Cl | —CH₂CH(CH₃)Cl | 0 |
| 402 | H | —CH₂CH(CH₃)Cl | —CH₂CH(CH₃)Cl | 1 |
| 403 | H | —CH₂CH(CH₃)Cl | —CH₂CH(CH₃)Cl | 2 |
| 404 | H | —CH₂CH(CH₃)Cl | —Ph | 0 |
| 405 | H | —CH₂CH(CH₃)Cl | —Ph | 1 |
| 406 | H | —CH₂CH(CH₃)Cl | —Ph | 2 |
| 407 | H | —CH₂CH(CH₃)Cl | —C(CH₃)₃ | 0 |
| 408 | H | —CH₂CH(CH₃)Cl | —C(CH₃)₃ | 1 |
| 409 | H | —CH₂CH(CH₃)Cl | —C(CH₃)₃ | 2 |
| 410 | H | —C(CH₃)₃ | —CH₂CH₂Cl | 0 |
| 411 | H | —C(CH₃)₃ | —CH₂CH₂Cl | 1 |
| 412 | H | —C(CH₃)₃ | —CH₂CH₂Cl | 2 |
| 413 | H | —C(CH₃)₃ | —CH₂CH(CH₃)Cl | 0 |
| 414 | H | —C(CH₃)₃ | —CH₂CH(CH₃)Cl | 1 |
| 415 | H | —C(CH₃)₃ | —CH₂CH(CH₃)Cl | 2 |
| 416 | H | —Ph | —CH₂CH₂Cl | 0 |
| 417 | H | —Ph | —CH₂CH₂Cl | 1 |
| 418 | H | —Ph | —CH₂CH₂Cl | 2 |
| 419 | H | —Ph | —CH₂CH(CH₃)Cl | 0 |
| 420 | H | —Ph | —CH₂CH(CH₃)Cl | 1 |
| 421 | H | —Ph | —CH₂CH(CH₃)Cl | 2 |
| 422 | —CH₂O—CH₂CH₂— | | —CH₂CH₂OH | 0 |
| 423 | —CH₂O—CH₂CH₂— | | —CH₂CH₂OH | 1 |
| 424 | —CH₂O—CH₂CH₂— | | —CH₂CH₂OH | 2 |
| 425 | —CH₂O—CH₂CH₂— | | —CH₂CH(CH₃)OH | 0 |
| 426 | —CH₂O—CH₂CH₂— | | —CH₂CH(CH₃)OH | 1 |
| 427 | —CH₂O—CH₂CH₂— | | —CH₂CH(CH₃)OH | 2 |
| 428 | —CH₂O—CH₂CH₂— | | —CH₂CH₂Cl | 0 |
| 429 | —CH₂O—CH₂CH₂— | | —CH₂CH₂Cl | 1 |
| 430 | —CH₂O—CH₂CH₂— | | —CH₂CH₂Cl | 2 |
| 431 | —CH₂O—CH₂CH₂— | | —CH₂CH(CH₃)Cl | 0 |
| 432 | —CH₂O—CH₂CH₂— | | —CH₂CH(CH₃)Cl | 1 |
| 433 | —CH₂O—CH₂CH₂— | | —CH₂CH(CH₃)Cl | 2 |

EXAMPLE 434

90 g of the compound of the formula

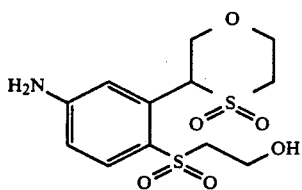

were added at 0°-10° C. to 360 g of chlorosulfonic acid and the mixture was stirred at 20°-25° C. for 5 hours. The mixture was discharged onto 900 ml of ice-water, and spontaneous crystallization took place. The precipitate was filtered off, washed with acetone until free of sulfuric acid and dried. The yield was almost quantitative. The product conformed to the formula

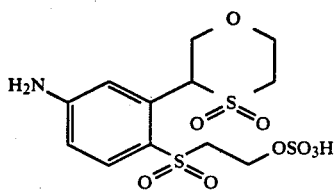

By the same method it is possible to obtain the compounds listed in Table 19.

TABLE 19

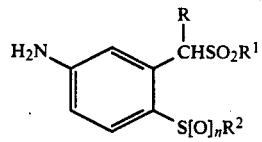

| Example No. | R | $R^1$ | $R^2$ | n |
|---|---|---|---|---|
| 435 | H | —CH$_2$CH$_2$OSO$_3$H | —C(CH$_3$)$_3$ | 0 |
| 436 | H | —CH$_2$CH$_2$OSO$_3$H | —C(CH$_3$)$_3$ | 1 |
| 437 | H | —CH$_2$CH$_2$OSO$_3$H | —C(CH$_3$)$_3$ | 2 |
| 438 | H | —CH$_2$CH$_2$OSO$_3$H | —Ph | 0 |
| 439 | H | —CH$_2$CH$_2$OSO$_3$H | —Ph | 1 |
| 440 | H | —CH$_2$CH$_2$OSO$_3$H | —Ph | 2 |
| 441 | H | —CH$_2$CH(CH$_3$)OSO$_3$H | —C(CH$_3$)$_3$ | 0 |
| 442 | H | —CH$_2$CH(CH$_3$)OSO$_3$H | —C(CH$_3$)$_3$ | 1 |
| 443 | H | —CH$_2$CH(CH$_3$)OSO$_3$H | —C(CH$_3$)$_3$ | 2 |
| 444 | H | —CH$_2$CH(CH$_3$)OSO$_3$H | —Ph | 0 |
| 445 | H | —CH$_2$CH(CH$_3$)OSO$_3$H | —Ph | 1 |
| 446 | H | —CH$_2$CH(CH$_3$)OSO$_3$H | —Ph | 2 |
| 447 | H | —C(CH$_3$)$_3$ | —CH$_2$CH$_2$OSO$_3$H | 0 |
| 448 | H | —C(CH$_3$)$_3$ | —CH$_2$CH$_2$OSO$_3$H | 1 |
| 449 | H | —C(CH$_3$)$_3$ | —CH$_2$CH$_2$OSO$_3$H | 2 |
| 450 | H | —C(CH$_3$)$_3$ | —CH$_2$CH(CH$_3$)OSO$_3$H | 0 |
| 451 | H | —C(CH$_3$)$_3$ | —CH$_2$CH(CH$_3$)OSO$_3$H | 1 |
| 452 | H | —C(CH$_3$)$_3$ | —CH$_2$CH(CH$_3$)OSO$_3$H | 2 |
| 453 | H | —Ph | —CH$_2$CH$_2$OSO$_3$H | 0 |
| 454 | H | —Ph | —CH$_2$CH$_2$OSO$_3$H | 1 |
| 455 | H | —Ph | —CH$_2$CH$_2$OSO$_3$H | 2 |
| 456 | H | —Ph | —CH$_2$CH(CH$_3$)OSO$_3$H | 0 |
| 457 | H | —Ph | —CH$_2$CH(CH$_3$)OSO$_3$H | 1 |
| 458 | H | —Ph | —CH$_2$CH(CH$_3$)OSO$_3$H | 2 |
| 459 | —CH$_2$O—CH$_2$CH$_2$— | | —CH$_2$CH(CH$_3$)OSO$_3$H | 0 |
| 460 | —CH$_2$O—CH$_2$CH$_2$— | | —CH$_2$CH(CH$_3$)OSO$_3$H | 1 |
| 461 | —CH$_2$O—CH$_2$CH$_2$— | | —CH$_2$CH(CH$_3$)OSO$_3$H | 2 |
| 462 | —CH$_2$OCH$_2$CH$_2$— | | —CH$_2$CH$_2$OSO$_3$H | 0 |
| 463 | —CH$_2$OCH$_2$CH$_2$— | | —CH$_2$CH$_2$OSO$_3$H | 1 |

EXAMPLE 464

32 g of the compound of the formula

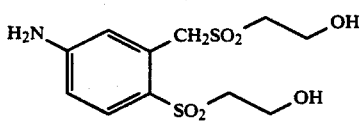

described in Example 350 were added at 0°-10° C. to 120 g of chlorosulfonic acid and the mixture was stirred at 20°-25° C. for 2 hours. Discharging the mixture onto 300 g of ice-water left the product of the formula

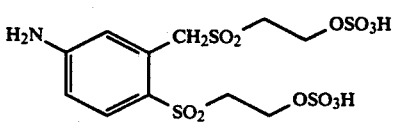

in solution. If the sulfuric ester was used for diazotization reactions, the diazotization was carried out from a sulfuric acid solution. For condensation with heterocyclic attachment components, the sulfuric acid solution was neutralized with sodium bicarbonate and further reacted as a solution.

The same method can be used to obtain the following compounds of the general formula:

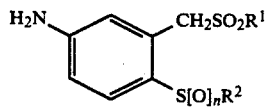

TABLE 20

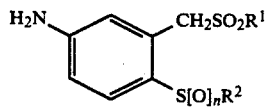

| Ex. No. | $R^1$ | $R^2$ | n |
|---|---|---|---|
| 465 | —CH$_2$CH$_2$OSO$_3$H | —CH$_2$CH$_2$OSO$_3$H | 0 |
| 466 | —CH$_2$CH$_2$OSO$_3$H | —CH$_2$CH$_2$OSO$_3$H | 1 |
| 467 | —CH$_2$CH$_2$OSO$_3$H | —CH$_2$CH(CH$_3$)OSO$_3$H | 0 |
| 468 | —CH$_2$CH$_2$OSO$_3$H | —CH$_2$CH(CH$_3$)OSO$_3$H | 1 |
| 469 | —CH$_2$CH$_2$OSO$_3$H | —CH$_2$CH(CH$_3$)OSO$_3$H | 2 |
| 470 | —CH$_2$CH(CH$_3$)OSO$_3$H | —CH$_2$CH(CH$_3$)OSO$_3$H | 0 |
| 471 | —CH$_2$CH(CH$_3$)OSO$_3$H | —CH$_2$CH(CH$_3$)OSO$_3$H | 1 |
| 472 | —CH$_2$CH(CH$_3$)OSO$_3$H | —CH$_2$CH(CH$_3$)OSO$_3$H | 2 |
| 473 | —CH$_2$CH(CH$_3$)OSO$_3$H | —CH$_3$CH$_2$OSO$_3$H | 0 |
| 474 | —CH$_2$CH(CH$_3$)OSO$_3$H | —CH$_3$CH$_2$OSO$_3$H | 1 |
| 475 | —CH$_2$CH(CH$_3$)OSO$_3$H | —CH$_3$CH$_2$OSO$_3$H | 2 |

We claim:

1. A double attachment reactive dye of the formula (I):

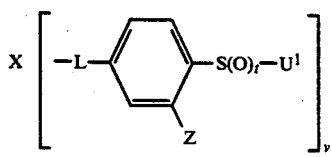

wherein
$U^1$ is $C_1$-$C_4$-alkyl, phenyl, $C_2$-$C_{10}$-alkenyl or a radical of the formula:

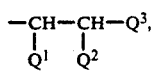

wherein $Q^1$ and $Q^2$ are identical or different and each is independently of the other hydrogen or $C_1$–$C_4$-alkyl, and $Q^3$ is a group which is detachable under alkaline reaction conditions, Z is the radical of the formula:

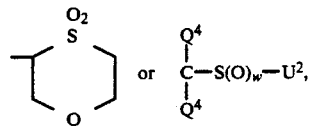

wherein $Q^4$ is, independently of the other, hydrogen or $C_1$–$C_4$-alkyl which is unsubstituted or substituted by cyano; $U^2$ is $C_1$–$C_4$-alkyl, phenyl, $C_2$–$C_{10}$-alkenyl or a radical of the formula:

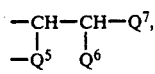

wherein $Q^5$ and $Q^6$ are identical or different and each is, independently of the other, hydrogen or $C_1$–$C_4$-alkyl, and $Q^7$ is a group which is detachable under alkaline reaction conditions, and w is 2, t is 2, v is 1 or 2, X is a) a radical of a chromophore which either does not have a further reactive group or which does have a further reactive group, and which is derived from a mono- or disazo dye or a copper formazan, or b) a radical of a coupling component which additionally may be linked to the radical of a diazo component via an azo bridge and which may additionally have a reactive group, and L is a) a bridge member of the formula:

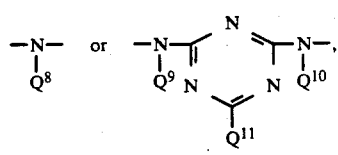

wherein $Q^8$ is hydrogen or $C_1$–$C_4$-alkyl, $Q^9$ and $Q^{10}$ are identical or different and each is independently of the other hydrogen or $C_1$–$C_4$-alkyl, and $Q^{11}$ is fluorine, chlorine or bromine; or b) an azo bridge, with the proviso that at least one of the two radicals $U^1$ and $U^2$ is not $C_1$–$C_4$-alkyl or phenyl.

2. The double attachment reactive dye as claimed in claim 1, of the formula (Ia):

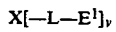

wherein X, L and v are each as defined in claim 1, and $E^1$ is a radical of the formula (IIa):

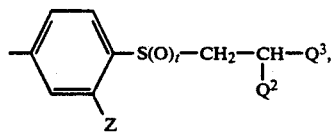

wherein $Q^2$ is hydrogen or methyl, $Q^3$ is $OSO_3H$,

Z is the radical of the formula:

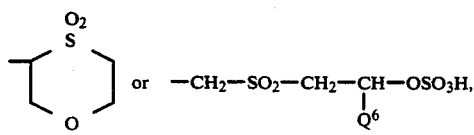

wherein $Q^6$ is hydrogen or methyl.

3. The double attachment reactive dye as claimed in claim 1, of the formula (Ib):

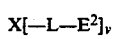

wherein X, L and v are each as defined above and $E^2$ is a radical of the formula (IIb):

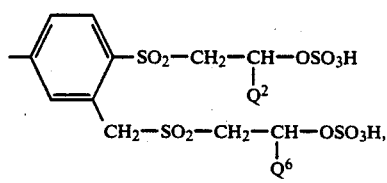

wherein $Q^2$ and $Q^6$ are each, independently of the other, hydrogen or methyl.

4. The double attachment reactive dye as claimed in claim 1, of the formula (Ic):

wherein X, L and v are each as defined above and $E^3$ is a radical of the formula (IIc):

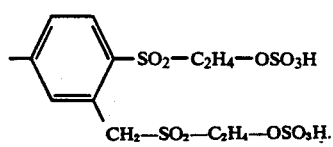

* * * * *